(12) United States Patent
Velasco Alvarez et al.

(10) Patent No.: US 6,815,189 B1
(45) Date of Patent: Nov. 9, 2004

(54) **GENE FROM *ACREMONIUM CHRYSOGENUM* ENCODING A PROTEIN WITH CEPHALOSPORIN C ACETYLHYDROLASE ACTIVITY AND METHODS OF USE OF SUCH GENE**

(75) Inventors: Javier Velasco Alvarez, Leon (ES); Santiago Gutierrez Martin, Leon (ES); Francisco Javier Casqueiro Blanco, Leon (ES); Sonia Campoy Garcia, Leon (ES); Francisco Fierro Fierro, Leon (ES); Jose Luis Barredo Fuente, Leon (ES); Bruno Diez Garcia, Leon (ES); Juan Francisco Martin Martin, Leon (ES)

(73) Assignee: Antibiotics, S.A.U., Leon (ES)

( * ) Notice: Subject to any disclaimer, the term of this patent is extended or adjusted under 35 U.S.C. 154(b) by 0 days.

(21) Appl. No.: 09/958,413
(22) PCT Filed: Apr. 7, 2000
(86) PCT No.: PCT/ES00/00126
§ 371 (c)(1), (2), (4) Date: Mar. 1, 2002
(87) PCT Pub. No.: WO00/61767
PCT Pub. Date: Oct. 19, 2000

(30) Foreign Application Priority Data

Apr. 9, 1999 (ES) .............................................. 9900731

(51) Int. Cl.$^7$ .............................. C12N 9/14; C12N 1/20; C12N 15/63; C07N 21/04; C12P 1/00; C12P 35/02
(52) U.S. Cl. ............... 435/196; 435/252.3; 435/252.33; 435/320.1; 435/47; 435/51; 536/23.2
(58) Field of Search .............................. 435/196, 252.3, 435/252.33, 320.1, 47, 51; 536/23.2

(56) References Cited

FOREIGN PATENT DOCUMENTS

| EP | 0454478 | 10/1991 |
|----|---------|---------|
| WO | 9955881 | 11/1999 |

OTHER PUBLICATIONS

Samal et al 1993 EMBL Acc# M54901 alignment with SEQ ID No.: 4.*
Leger et al 1999 EMBL Acc# M73795 alignment with SEQ ID No.: 5.*
Gunkel et al 1995 EMBL Acc# X14688 alignment with SEQ ID No.: 6.*
Fujisawa, Y. et al. "Deacetylcephalosporin C Formation by Cephalosporin C Acetyl–hydrolase induced in a *Cephalosporium acermonium* Mutant" *Agr. Biol. Chem.*, vol 39, No. 6, p. 1303–1309, (1975).
Fujisawa, Y. et al. "New Findings on Cephalosporin C Biosynthesis" *Nature New Biology*, vol. 246, p. 154–155, (1973).
Hinnen, A., et al. "Enzymatic Hydrolysis of Cephalosporin C by an Extracellular Acetylhydrolase of *Cephalosporium acermonium* " *Antimacrobial Agents and Chem.*, vol. 9, No. 5, p. 824–830, (1976).
Choi, S–H., et al. "Regulation of Cephalosporin C Acetyl–hydrolase in Cephalosporin C Fermentation by *Cephalosporium acermonium* M–113" *Kor. J. Appl. Microbiol. Bioeng.*, vol. 14, No. 1, p. 51–55, (1986).

* cited by examiner

Primary Examiner—Rebecca E. Prouty
Assistant Examiner— Swope
(74) Attorney, Agent, or Firm—Ladas & Parry, LLP

(57) ABSTRACT

An isolated DNA sequence that encodes a peptide with CPC-acetylhydrolase enzymatic activity is disclosed. Also, a method of expressing CPC-acetylhydrolase activity that includes the steps of (a) providing a microorganism that is susceptible to transformation with the isolated DNA sequence and that, upon transformation, expresses the CPC-acetylhydrolase activity encoded by the sequence, and (b) transforming the microorganism with the DNA sequence to cause expression of the CPC-acetylhydrolase activity in the microorganism is disclosed. Also, a method for producing a microorganism with increased capacity to aid in the production of cephalosporin, which method includes the steps of (a) providing a microorganism that has CPC-AH activity by virtue of expression of the DNA sequence or of a fragment thereof coding for the CPC-acetylhydrolase enzyme activity; and (b) inactivating the activity by disrupting expression of the DNA sequence is disclosed.

21 Claims, 12 Drawing Sheets

FIGURE 1
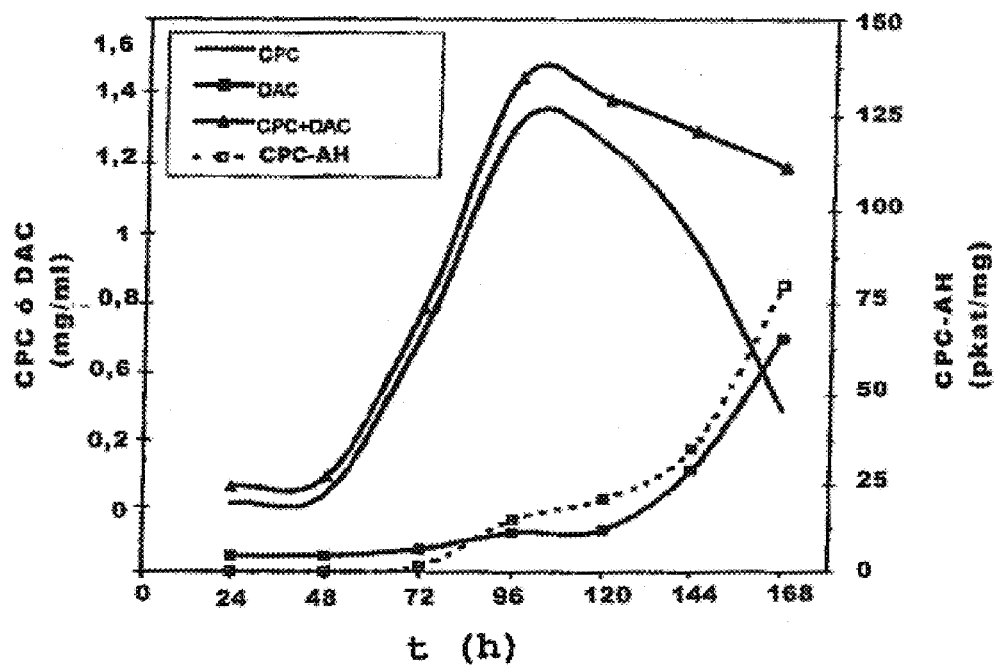
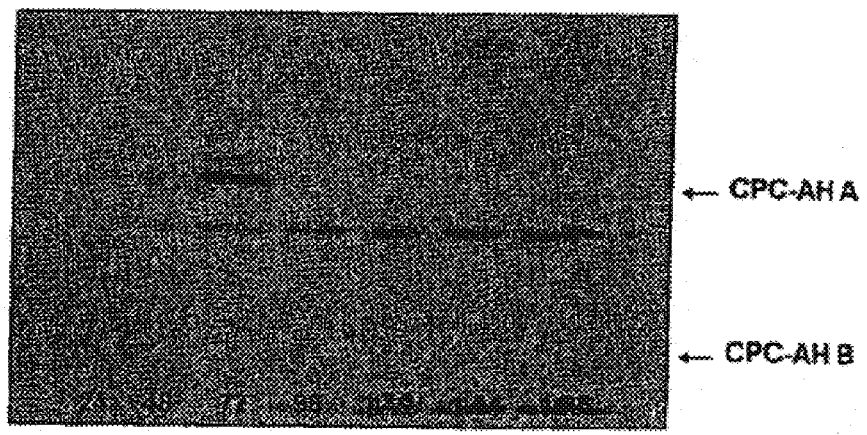

FIGURE 4
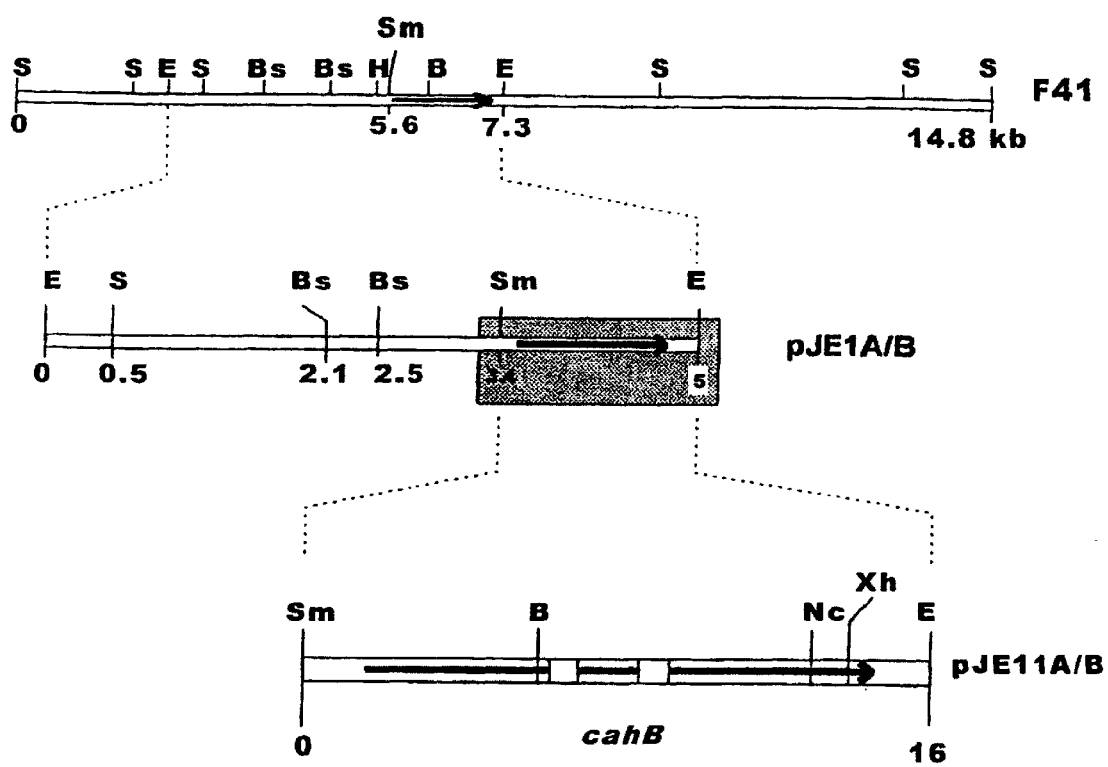
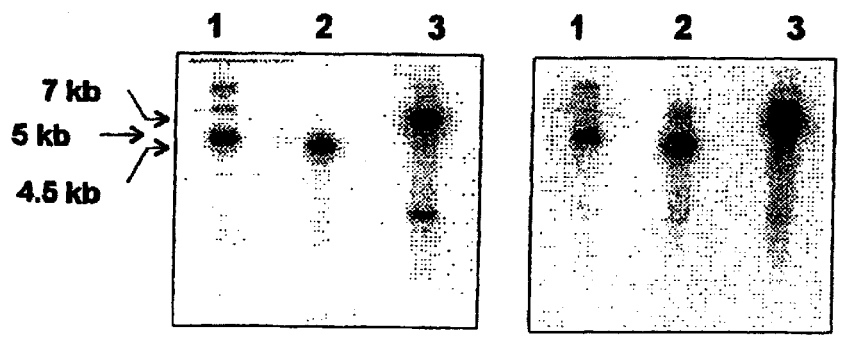

FIGURE 11
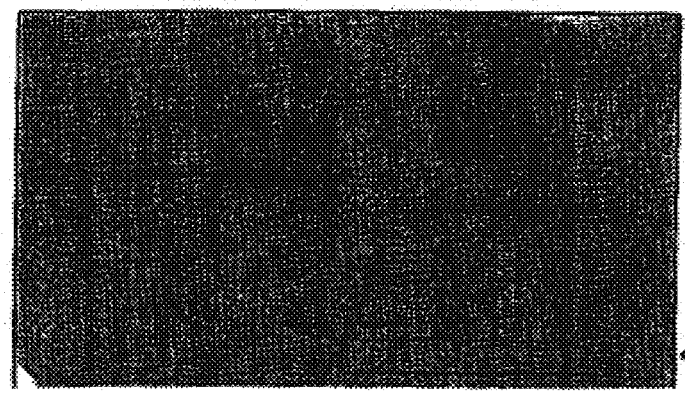

GENE FROM *ACREMONIUM CHRYSOGENUM* ENCODING A PROTEIN WITH CEPHALOSPORIN C ACETYLHYDROLASE ACTIVITY AND METHODS OF USE OF SUCH GENE

An extracellular protease of *Acremonium chrysogenum* with CPC-acetylhydrolase activity and its use for the synthesis of deacetylated derivatives of cephalosporin C and inactivation of the gene for increasing the yield of cephalosporin.

FIELD OF THE INVENTION

The present invention includes the identification of a protein with CPC-acetylhydrolase (CPC-AH) activity secreted by the fungus *Acremonium chrysogenum*, purification of the said protein, cloning of the gene that codes for the said enzyme and the inactivation of this gene by genetic methods. In addition it proposes use of the enzyme for the preparation of deacetylated derivatives of cephalosporin C and 7-aminocephalosporanic acid (7-ACA), such as deacetylcephalosporin C (DAC) and deacetyl 7-ACA. These compounds can be used as starting material for the synthesis of some derivatives of cephalosporin of commercial interest.

In industrial fermentations of *A. chrysogenum* for the production of cephalosporin, accumulation of DAC in the culture media is observed. This accumulation is due on the one hand to insufficient acetylation of the DAC and on the other hand to chemical and enzymatic deacetylation of the CPC formed. Inactivation by using recombinant DNA techniques of the gene cahB, which codes for the enzyme CPC-AH B, partly prevents accumulation of DAC during fermentation.

BACKGROUND OF THE INVENTION

The production of deacetylcephalosporin C (called DAC hereinafter) from cephalosporin C (called CPC hereinafter) is effected by eliminating the acetyl residue at the 3' carbon of the CPC molecule. This conversion can be carried out by chemical or enzymatic methods. Advantages of the latter are that they can be effected in less drastic conditions of pH and temperature and in addition they produce fewer side reactions. The use of enzymes with cephalosporin C-acetylhydrolase (hereinafter referred to as CPC-AH) activity obtained from a variety of sources such as the peel of citrus fruits (Jeffery et al., 1961, Biochem. J. 81: 591–596), actinomycetes (Demain et al., 1963, J. Bacteriol. 35: 339–344), *Bacillus subtilis* (Abbott and Fukuda, 1975, Appl. Microbiol. 30: 413–419; Takimoto et al., 1994, J. Ferment. Bioeng. 77: 17–22), *Rodosporidium toruloides* (Politino et al., 1997, Appl. Env. Microbiol. 63: 4807–4811) and *Thermoanaerobium sp.* (Lorenz and Wiegel, 1997, J. Bacteriol. 179: 5436–5441), is known.

On the other hand, appreciable amounts of DAC have been detected both in intracellular extracts and in extracellular fluids of *A. chrysogenum*, the fungus used for the industrial production of CPC. The presence of this CPC precursor is undesirable because it lowers the final yields of CPC and hampers its purification. Various non-exclusive hypotheses have been proposed to explain the origin of this compound in the culture media: (I) Some of the DAC accumulated may originate from lack of acetylation of the biosynthetic intermediate, as it is known that there is a low level of expression of the cefG gene that codes for DAC-acetyltransferase (Velasco et al., 1994, J. Bacteriol. 176: 985–991). (II) The DAC may arise through chemical hydrolysis of CPC which is more evident at alkaline pH (Konecny et al., 1972, J. Antibiot. 26: 135–141). (III) The DAC may be synthesized by enzymatic hydrolysis, as extracellular CPC-AH activities have been described in fermentation media of *A. chrysogenum*. Fujisawa et al. (1975, Agric. Biol. Chem., 39: 1303–1309) described a mutant with CPC-AH activity. Shortly thereafter, Hinnen and Nüesch (1976, Antimicrob. Agents Chemother. 9: 824–830) purified an extracellular CPC-AH with low affinity for CPC ($k_M$ 20 mM) and whose synthesis is controlled by the carbon source. The purified CPC-AH had a molecular weight of approximately 25 kDa and an isoelectric point of 4.3. The enzyme was strongly inhibited by diisopropylfluorophosphate. However, these preliminary studies have not been followed by any description of more detailed data concerning the said activities, nor the cloning, characterization and use of the corresponding gene.

SUMMARY OF THE INVENTION

In accordance with the invention, there is provided an isolated DNA sequence comprising SEQ ID NO:4 or a fragment of SEQ ID NO:4 encoding a peptide with CPC-acetylhydrolase enzymatic activity.

There is also provided a method of expressing CPC-acetylhydrolase activity comprising:

(a) providing a microorganism that is susceptible to transformation with the isolated DNA sequence and that, upon transformation, expresses the CPC-acetylhydrolase activity encoded by said DNA sequence; and (b) transforming the microorganism with the DNA sequence to cause expression of the CPC-acetylhydrolase activity in the microorganism. In one embodiment, the method further comprises using the expressed CPC-acetylhydrolase activity to prepare a deacetylated derivative of cephalosporin C or 7-aminocephalosporanic acid. The derivative can be deacetylcephalosporin C or deacetyl 7-aminocephalosporanic acid.

There is further provided a method for producing a microorganism with increased capacity to aid in the production of cephalosporin comprising (a) providing a microorganism that has CPC-AH activity by virtue of expression of the DNA sequence or a fragment thereof coding for the CPC-acetylhydrolase enzymatic activity; and (b) inactivating said activity by disrupting expression of the DNA sequence.

BRIEF DESCRIPTION OF THE DRAWINGS

FIG. 1. A. Yield of CPC, DAC and total cephalosporins in a culture of *A. chrysogenum* C10 in the so-called fermentation medium and CPC-AH activity in media of the said culture. B. Staining of acetylhydrolase activity against β-naphthyl acetate of a polyacrylamide gel in which the proteins present in the culture supernatants of *A. chrysogenum* were separated at different fermentation times. The two bands of CPC-AH A and B activity are indicated by arrows on the right.

4: Active fractions after gel filtration on Sephadex G75. SF; 5: Active fractions after anion exchange chromatography on DEAE-Sepharose FF; 7: CPC-AH B purified after gel filtration on Superose 12 for FPLC.

Figure 3:
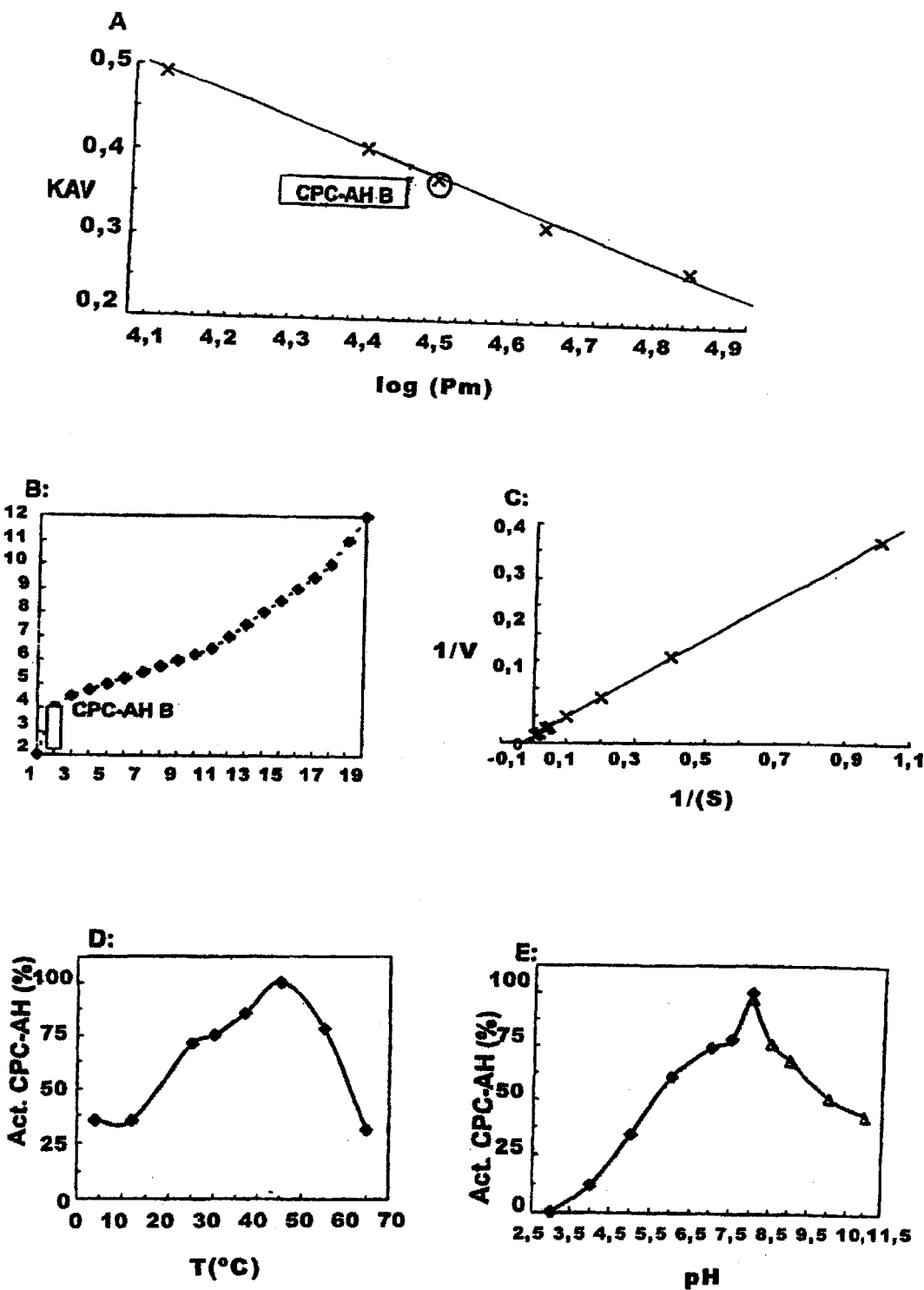

FIG. 3. Characterization of the protein CPC-AH B: A: Determination of molecular weight by gel filtration. Molecular weight markers from left to right: ribonuclease A, chymotrypsinogen, FGG albumin and seralbumin; B: Determination of the isoelectric point by preparative electrofocusing; C: Determination of $K_M$ and $V_{max}$ of CPC-AH B vs. CPC; D: Effect of temperature and E of pH on CPC-AH B activity.

FIG. 4: Part A: Restriction map of a 14.8 kb region of the DNA of *A. chrysogenum* cloned in phage F41 and containing the cahB gene (arrowed). The EcoRI fragment indicated by vertical lines was subcloned producing the plasmids pJE1A or pJE1B (in both orientations). The 1.6 kb fragment SmaI-EcoRI marked with a box was subcloned to produce the plasmids pJE11A or pJE11B (CECT 5067). The two breaks in the cahB gene correspond to two introns. Part B: Hybridization of the DNA of phage 41 digested with SalI (lane 1), SalI-EcoRI (lane 2) and EcoRI (lane 3) with the 0.7 kb probe internal to the cahB gene (on left) and with the 1.02 kb probe EcoRI-DraI corresponding to protease T of *Tritirachium album* (on right). The sizes of the hybridization bands (in kb) are indicated by arrows on the right.

Figure 5:
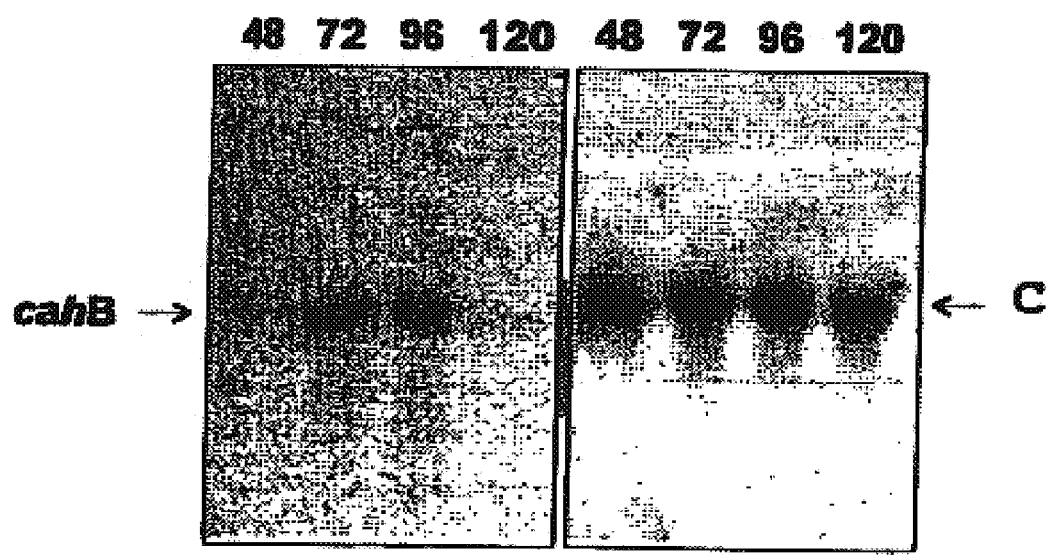

FIG. 5: Transcript of the cahB gene (1.4 kb) of *A. chrysogenum* (on left) in mycelium-collected at 48, 72, 996 and 120 [hours] of fermentation in conditions of production of cephalosporin. The transcripts of the gene that codes for β-actin (1.6 kb) in the same samples of RNA are shown (on the right) as a control (C).

Figure 6:
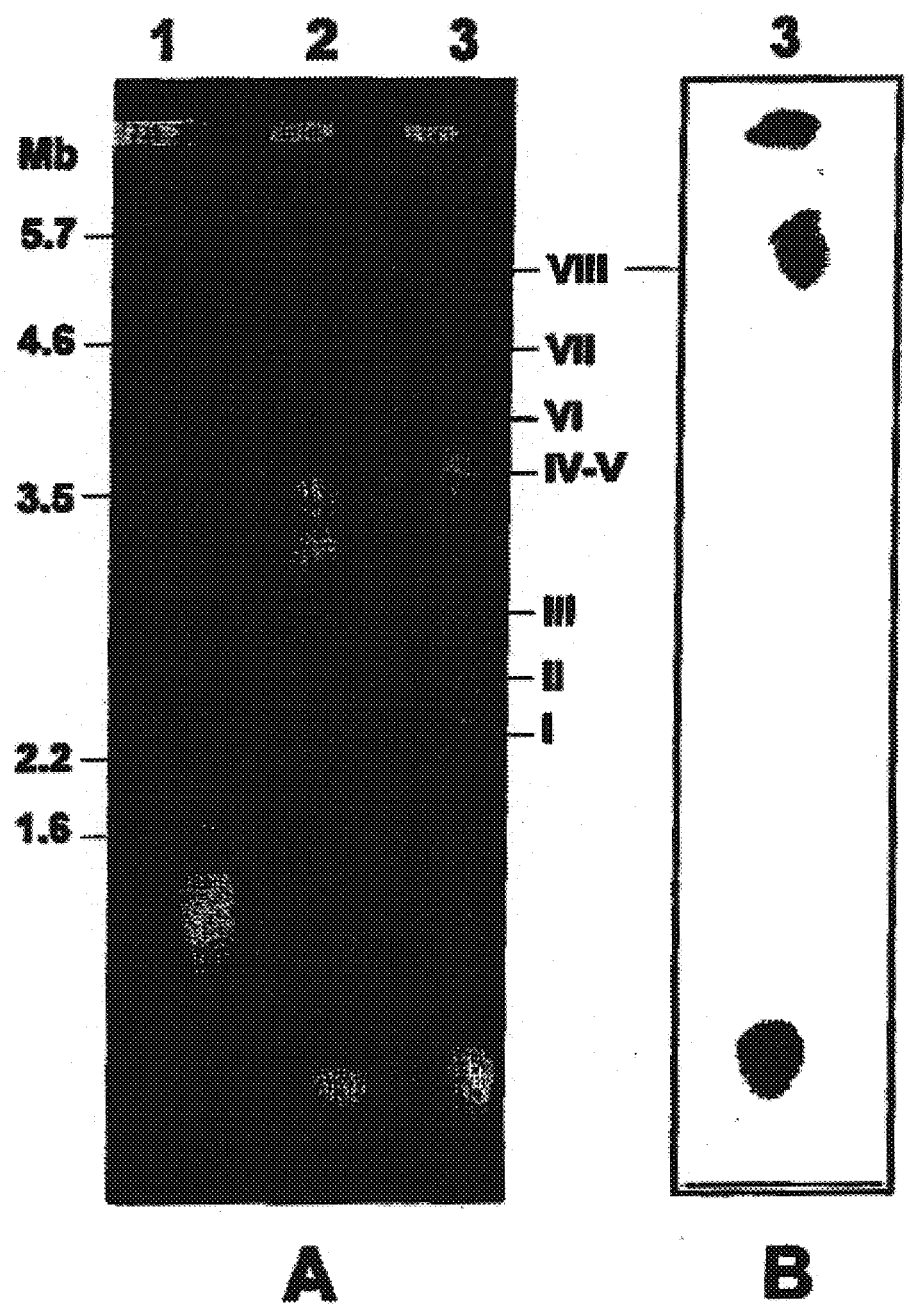

FIG. 6. A. Resolution of the chromosomes of *A. chrysogenum* C10 by pulsed-field gel electrophoresis. Lane 1: Markers of chromosome size (indicated in Mb on the left). The three larger markers are chromosomes of *Schizosaccharomyces pombe* and the two smaller ones are from *Saccharomyces cerevisiae*. Lane 2: Chromosomes from *A. nidulans* FGSC4 used as size markers: 5.0, 4.5, 4.1, 3.7 (doublet), 3.4 (doublet) and 2.4 Mb (Montenegro et al., 1992, J. Bacteriol. 174: 7063–7067). Lane 3: Chromosomes of *A. chrysogenum* C10 numbered from smaller to larger (right) B. Hybridization of the gel on the left with a 0.6 kb probe NcoI-BamHI internal to the cahB gene. The cahB gene is located in the smaller band (chromosome VIII of 5.5 Mb).

Figure 7:
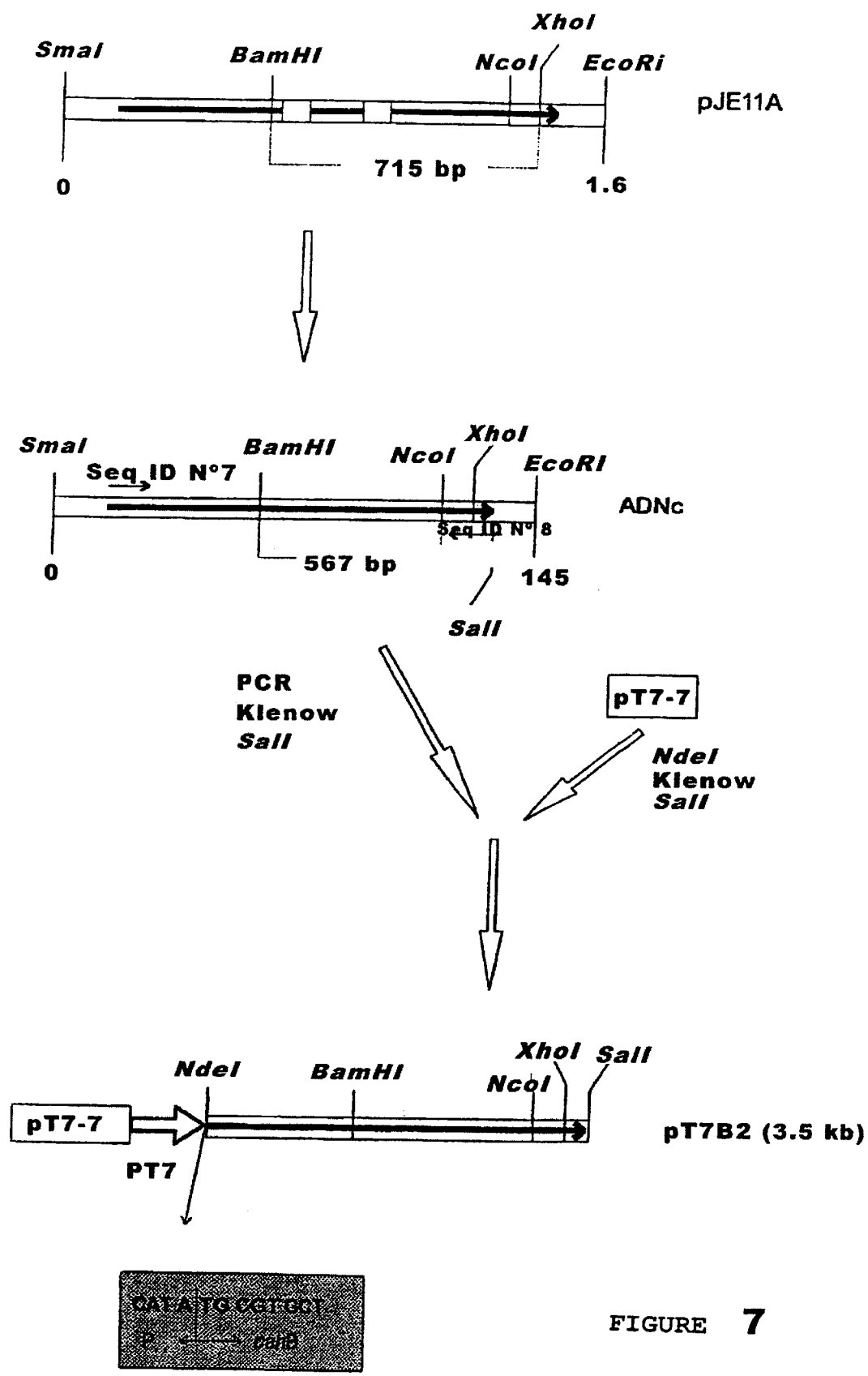

FIG. 7: Cloning of the cahB gene starting from a cDNA library and construction of plasmids for expression of CPC-AH B in *E. coli*.

Figure 8:
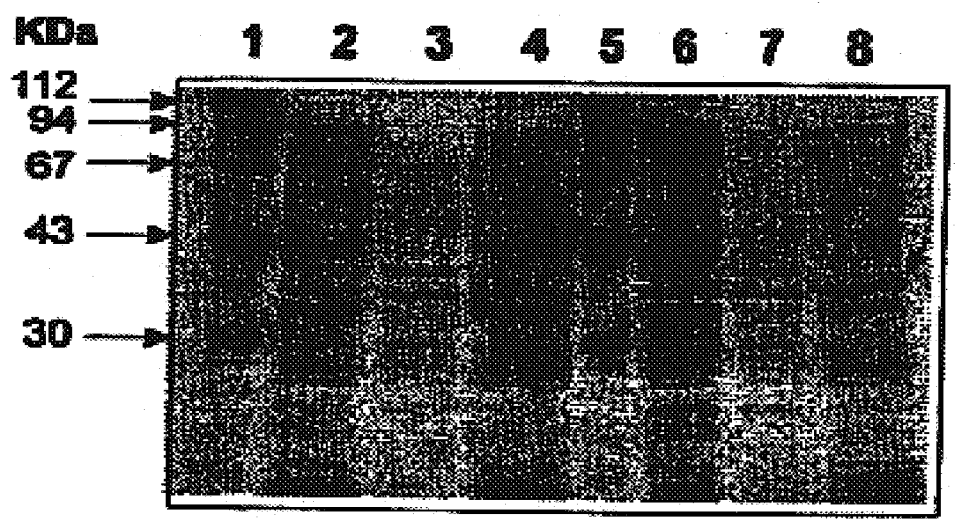

FIG. 8: SDS-PAGE of cellular extracts from the strains of *E. coli* that express the various forms of CPC-AH B. Lanes 1 and 5: Molecular weight markers (the sizes, of the markers in kDa are indicated by arrows on the left). 2: *E. coli* JM109(DE3)/pT7B2.1 Whole cells; 3: *E. coli* JM109(DE3)/pT7B2.1 Soluble extract; 4: *E. coli* JM109(DE3)/pT7B2.1 Insoluble fraction; 6: *E. coli* JM109(DE3)/pT7B2.2 Whole cells; 7: *E. coli* JM109(DE3)/pT7B2.2 Soluble extract; 8: *E. coli* JM109(DE3)/pT7B2.2 Insoluble fraction. The arrows in lanes 4 and 8 show the overexpressed proteins of 42 and 31 kDa respectively.

Figure 9:
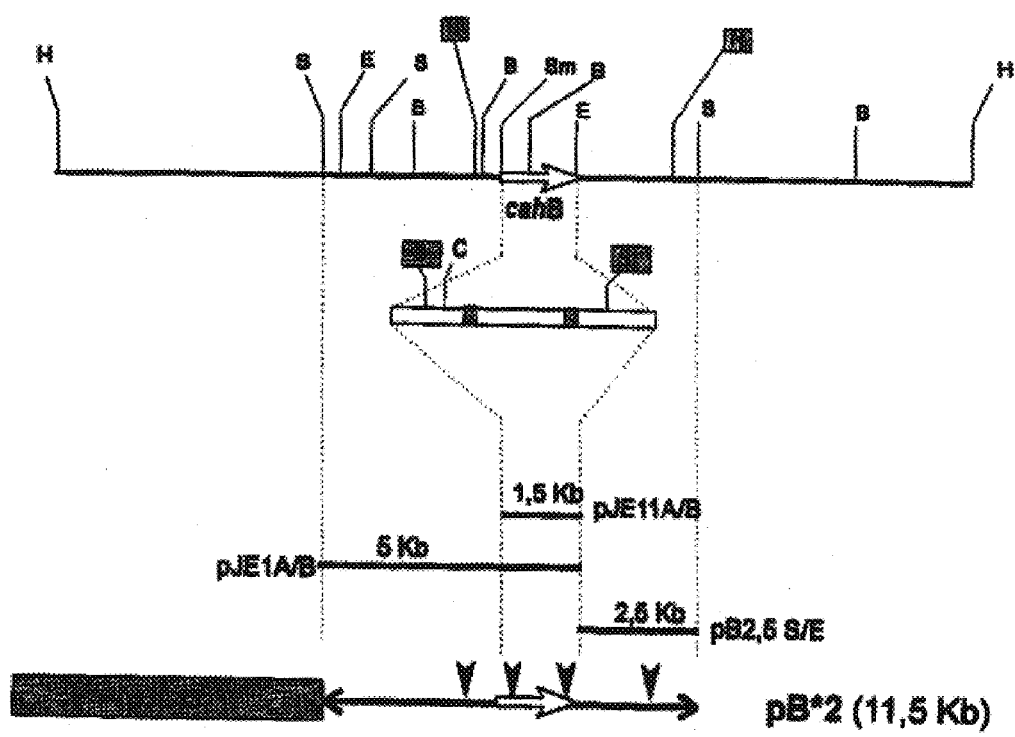

FIG. 9: Restriction map of the DNA fragment inserted in plasmid pJL43 for constructing plasmid pB*2. The positions of the restriction sites removed are indicated by vertical arrows in the lower part and their corresponding restriction sites are shown shaded.

B: BamHI; C: ClaI; E: EcoRI; H: HindIII; N: NotI; S: SalI; Sm: SmaI; St: StyI.

Figure 10:
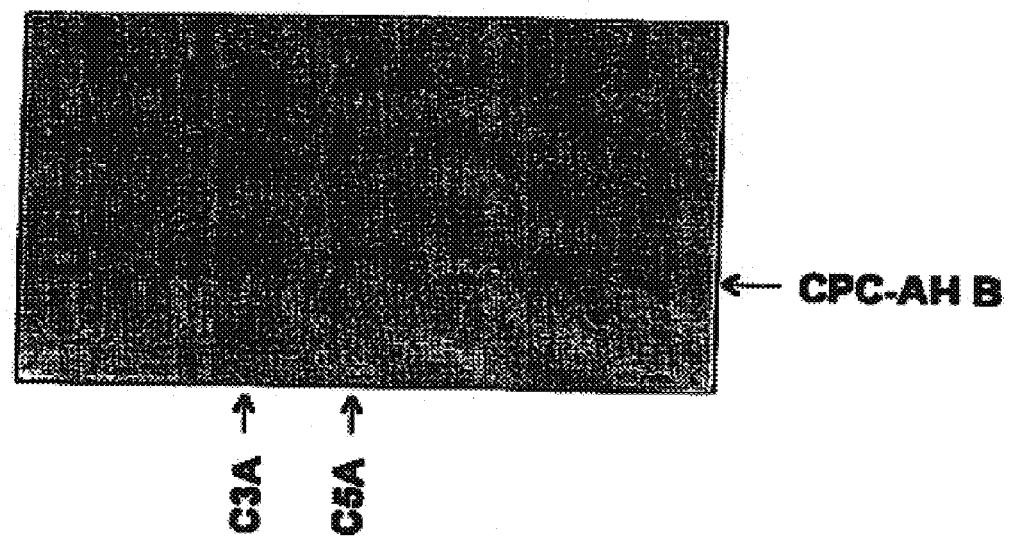

FIG. 10: Detection of CPC-AH activity in polyacrylamide gels in culture supernatants (168 hours) of various transformants of *A. chrysogenum* C10 obtained with plasmid pB*2. Arrows indicate the band corresponding to CPC-AH B activity and the transformants C3A and C5A used in subsequent studies.

FIG. 11: CPC-AH activities in the course of fermentation of *A. chrysogenum* C10 (part A) and the transformant C3A. (part B) in samples of culture medium taken every 24 hours. An arrow indicates the position of the CPC-AH B in strain C10 and a box indicates its absence in strain C3A.

Figure 12:
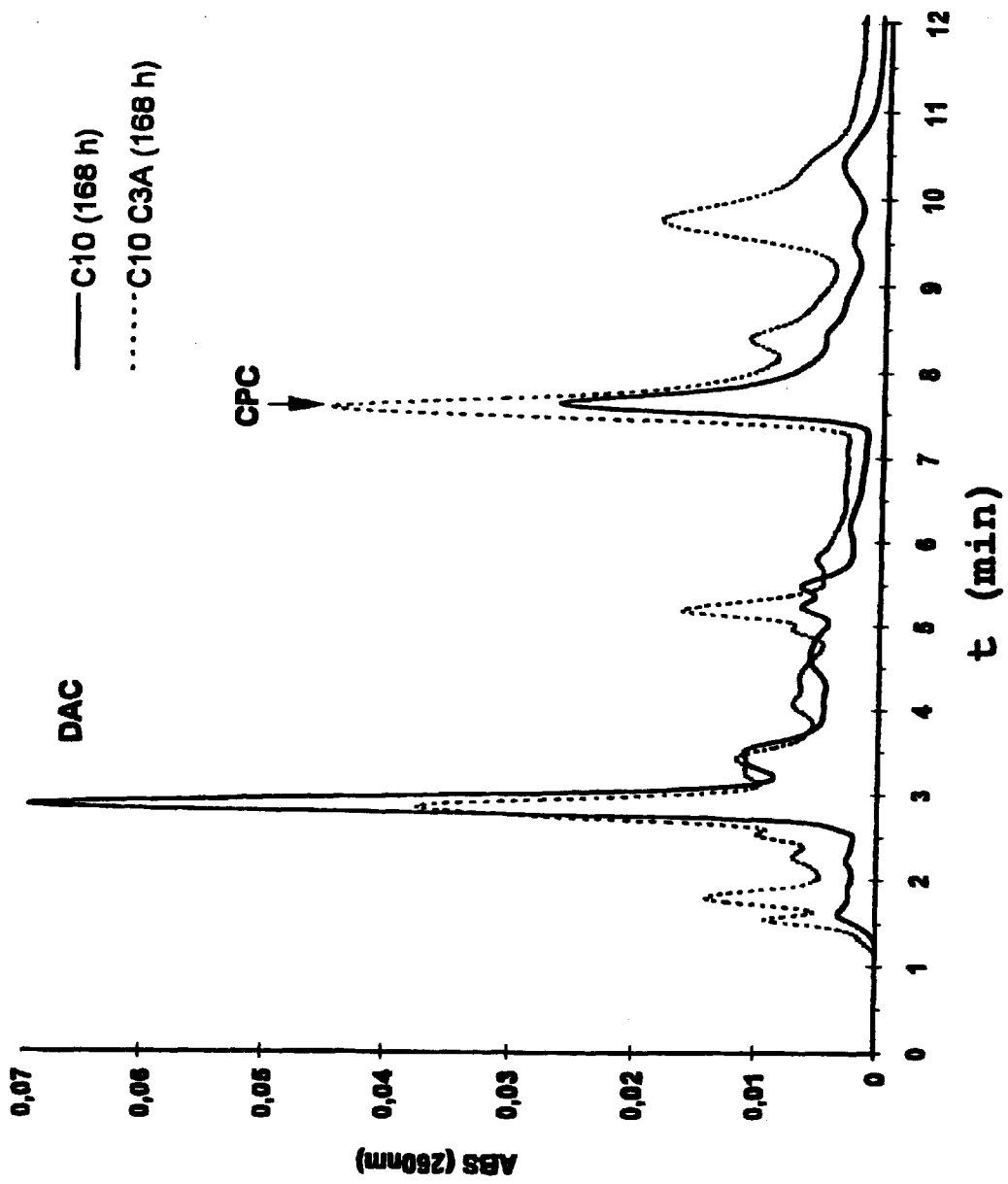

FIG. 12: HPLC analysis of the relative proportion of DAC and CPC in the strain *A. chrysogenum* C10 and in its transformant C3A in culture media taken at 168 hours of fermentation.

DETAILED DESCRIPTION OF THE INVENTION

For detection of CPC-AH activity, fermentation of the filamentous fungus *A. chrysogenum* C10 (ATCC 48272) was carried out in a defined medium and samples of the culture medium were taken every 24 hours. In these samples, on the one hand, CPC-AH activity was determined by means of a test using HPLC and on the other hand the presence of nonspecific acetylhydrolase activities was determined.

Enzymatic deacetylation (CPC-AH activity) was detected by mixing a solution of CPC (20 mM) with 75 μl of culture medium. Formation of DAC after one hour of incubation at 37° C. was analysed by HPLC. Activity appears in the culture media starting from 96 hours and increases gradually until it reaches a maximum at 168 hours of fermentation.

To elucidate whether the CPC-AH activity detected is due to one or more enzymes, the proteins present in the fermentation media were separated by electrophoresis in polyacrylamide gels that were developed in native conditions. Once separated, the enzymes with acetylhydrolase activity were detected by incubating the gels in a solution containing β-naphthyl acetate and Fast Blue RR. After stirring for 10 minutes, bands of a reddish colour appeared in the gel corresponding to the coprecipitation of naphthol and the Fast Blue in the zones where the acetylhydrolases are situated. In this way it was confirmed that at 168 hours (the time of maximum CPC-AH activity) at least two enzymes with acetylhydrolase activity appeared in the polyacrylamide gels and were designated CPC-AH A and CPC-AH B. To verify whether both enzymes are active against CPC, they were extracted from the gels and their activity was confirmed by HPLC.

The acetylhydrolase that displayed greater electrophoretic mobility (CPC-AH B) was purified from culture media collected at 168 hours of fermentation by fractional precipitation with ammonium sulphate, gel filtration chromatography, anion exchange chromatography and again gel filtration chromatography, this time at medium pressure. Kinetic studies were carried out on the purified enzyme, such as constant of affinity for CPC, maximum rate, optimum temperature and pH, effect on the activity of various metals and inhibitors and determination of molecular weight and isoelectric point.

A fraction of the purified protein was used for obtaining the amino acid sequence of its amino terminus. Analysis of the said sequence demonstrated its homology with protease T of the fungus *Tritirachium album*. As a function of the amino acid sequence and on the basis of the pattern of use of codons from genes of *A. chrysogenum*, a synthetic oligonucleotide was developed (SEQ ID NO: 2) which would hypothetically hybridize with the 5' end of the gene. In addition, a second oligonucleotide was synthesized (SEQ ID NO: 3), deduced by comparison with completely conserved zones of proteases similar to protease T of *T. album*.

Next, cloning of the gene corresponding to the CPC-AH B protein was tackled by hybridization with a gene library of strain *A. chrysogenum* C10 effected in the λEMBL3-ble substitution vector.

The aforementioned hybridization experiments were carried out with two probes of different origin:
  Probe 1: Fragment of 1020 pb EcoRI-DraI corresponding to the gene that codes for protease T of *T. album*.
  Probe 2: Fragment of 700 pb obtained by PCR, using as primers the oligonucleotides described in SEQ ID NO: 2 and SEQ ID NO: 3 and as complete DNA pattern of *A. chrysogenum* C10.

As a result a positive phage was purified and was studied in detail. Finally, a DNA fragment SmaI of approximately 1.6 kb was isolated, which presumably includes the gene cahB. Next, a total of 1621 pb was sequenced, including a 1295 pb reading frame interrupted by two introns of 68 and 78 pb, which coded for a protein of 383 amino acids. The amino acid sequence found in the mature protein corresponds to the amino acid sequence 107 to 127 of the protein deduced from the gene. This indicates formation of a preprotein that will be finally processed in the $Gln^{106}$ position to form the mature protein.

A series of searches carried out using the protein sequence databases (for example SwissProt) and in conceptual translation of DNA sequence databases (for example GenBank and EMBL) in the six possible reading frames, revealed significant similarities of the amino acid sequence with various proteases, especially with those of the subtilase family. Additionally, CPC-AH B possesses conserved sequences around the residues of histidine ($His^{176}$) and serine ($Ser^{331}$) typical of the serine proteases of the subtilase family. Therefore the enzyme is closely related to alkaline fungal proteases. In fact, purified CPC-AH B displays proteolytic activity.

TABLE 1

| 1. CPC-AH B A. chrysogenum | | | |
|---|---|---|---|
| 2. PROTT-TRI | 64.5% | | |
| 3. PROTK-TRI | 49.5% | 54.6% | |
| 4. PROTR-TRI | 48.4% | 52.2% | 85.2% |
| | 1. CPC-AH B A. chrysogenum | 2. PROTT-TRI | 3. PROTK-TRI |

Comparison of the protein CPC-AH B (1) with other proteins collected in the SwissProt database: (2) PROTT-TRI: Preprotease T from *Tritirachium album* (Samal et al. 1989, Gene, 85: 329–333). (3) PROTK-TRI: Preendoprotease K from *Tritirachium album* (Paehler et al. 1984, EMBO J. 3: 1311–1314); (4) PROTR-TRI: Preprotease R from *Tritirachium album* (Samal et al. 1990, Mol. Microbiol. 4: 1789–1792). Percentage of identity between the four sequences analysed.

Various groups of acetylhydrolases (esterases) and lipases display a high degree of conservation in the sequence and three-dimensional structure of the active centre with proteases and β-lactamases (Cygler et al., 1993, Protein Science 2: 366–382). Some authors have suggested that various groups of enzymes with serine in their active centre, including esterases, lipases, proteases, β-lactamases and proteins that bind to penicillin (PBPs) are derived from a common ancestral gene (Brenner, 1988, Nature, 334: 528–530). Although these enzymes recognize different substrates, important homologies have been found in the sequence between members of each group.

The genes involved in the biosynthesis of cephalosporin are grouped in the genome of *A. chrysogenum* in two clusters. With the aim of determining whether the cahB gene is located in one of these groups, the chromosomes that constitute the genome of *A. chrysogenum* were separated using the CHEF technique, were transferred onto filters and were hybridized with the aforementioned 1020 pb fragment EcoRI-DraI. In this way it was established that the cahB gene is located in the larger chromosome (VIII), whereas the cluster of early genes (pcbAB-pcbC) is found in chromosome VII and that of late genes (cefEF-cefG) in chromosome I, suggesting that the origin of the cahB gene is unrelated to that of the genes of cephalosporin biosynthesis.

To obtain the CPC-AH B protein in large quantity, expression of the cahB gene in *Escherichia coli* was proposed. Since the cahB gene has two introns it was necessary to clone the gene from a cDNA library. For this purpose, a cDNA library was constructed from the mRNA of the strain *A. chrysogenum* C10. This library was screened with the aforementioned 700 pb probe internal to the cahB gene, which permitted the purification and characterization of the DNA of a series of positive phages.

Using the gene in the form of cDNA, two constructions were performed: one for expression of the complete protein including the leader peptide (pT7B2.1) and the other for formation of the mature protein (pT7B2.2) in *E. coli* JM109 (DE3). Production of these heterologous proteins in *E. coli* was analysed by denaturing polyacrylamide gel electrophoresis (SDS-PAGE). The *E. coli* strain JM109 (DE3)/pT7B2.1 synthesizes an additional protein of 42 kDa whereas *E. coli* JM109 (DE3)/pT7B2.2 displays a protein of 31 kDa. The transformants of *E. coli* JM109(DE3)/pT7B2.2 displayed weak CPC-AH activity, whereas this enzymatic activity was not detected in those of *E. coli* JM109(DE3)/pT7B2.1.

The CPC-AH B obtained from *E. coli* JM109(DE3)/pT7B2.2 was used in reactions of deacetylation of CPC, demonstrating its usefulness in processes of this type. The parent strain of this clone, *E. coli* DH5α/PJE11B was deposited in the Spanish Collection of Standard Cultures (Colección Española de Cultivos Tipo, CECT), University of Valencia, Research Block, Burjasot Campus, 46100 Burjasot (Valencia) under No. 5067.

On the other hand, the accumulation of DAC in the culture media of *A. chrysogenum* suggests a decline in the level of production of CPC. A fraction of this accumulated DAC is due to enzymatic deacetylation of the CPC by extracellular CPC-AH enzymes. Inactivation, by means of recombinant DNA techniques, of the genes that code for these enzymes might prevent the enzymatic deacetylation of CPC during fermentation, with a consequent increase in the yields obtained.

With the aim of inactivating the gene that codes for CPC-AH B we employed the technique of gene disruption by simple integration. In this process we endeavour to generate two mutated gene copies, which is achieved when recombination occurs between an internal fragment of the target gene located in a plasmid, and the endogenous gene. To promote homologous recombination, a genomic DNA fragment larger than the cahB gene (7 kb) was employed for constructing the plasmid.

For the two copies of the mutated target gene to be generated, it is necessary to introduce two mutations into the gene located in the plasmid and in addition it is necessary for recombination to take place between these two points. For this, two mutations were generated at the 5' end of the gene, a restriction cut BamHI was eliminated, a KpnI cut was eliminated and a mutation was introduced into the StyI cut at the 3' end of the gene. The 7 kb fragment with the mutations was inserted in the plasmid pJL43 giving rise to the plasmid pB*2. To promote recombination, digestion was effected with ClaI, the restriction site located between the two mutations introduced into the gene.

The plasmid pB*2 was transformed in *A. chrysogenum* C10 and the transformants were selected in TSA medium supplemented with saccharose (10.3%) and phleomycin (40 µg/ml). The transformants obtained were fermented in MDFA, collecting samples of the culture medium every 24 hours. The presence of acetylhydrolase activities in the samples taken at 168 hours was analysed by means of native polyacrylamide gels. At least 3 of the 10 transformants analysed lack CPC-AH B activity.

To check whether the absence of CPC-AH B activity in one of the transformants selected (C3A) occurs throughout the fermentation, the supernatants collected every 24 hours both from this transformant and from the parent strain *A. chrysogenum* C10 were analysed. The band of CPC-AH B activity did not appear in any of the samples analysed, whereas the electrophoresis pattern of the acetylhydrolase residue remained similar to that of the control strain C10.

Absence of CPC-AH B activity in the C3A transformant is manifested as a change in the proportion of DAC and CPC in the culture media collected at 168 hours. On analysing these media by HPLC, it is observed that the concentration of CPC is greater in the transformant with the inactivated cahB gene than in the C10 strain without transformation, whereas the concentration of DAC decreases appreciably in the transformant. This transformed strain of *A. chrysogenum* was deposited in the Spanish Collection of Standard Cultures (CECT), University of Valencia, Research Block, Burjasot Campus, 46100 Burjasot (Valencia) under No. 20305.

EXAMPLE 1

1.1. Purification of the Enzyme CPC-AH B 1.1.1. Determination of CPC-AH Activities in Culture Supernatants of *Acremonium chrysogenum* C10

For fermentation of *A. chrysogenum* C10, plates of LPE solid medium were seeded (Le Page and Campbell, 1946, J. Biol. Chem. 162: 163–171) and were incubated for 7 days at 28° C. until a sporulated lawn culture was obtained. Fermentation in liquid medium was initiated by inoculating the spores obtained from three plates in a 500-ml indented flask containing 100 ml of so-called inoculation medium. This flask is incubated for 48 hours at 25° C. and 250 rev/min to obtain an abundant vegetative mycelium. Fermentation in conditions of production of antibiotics is initiated on inoculating 5 ml of the above vegetative culture in another 500 ml indented flask with 100 ml of so-called fermentation medium. This culture was incubated for 168 hours (7 days) at 25° C. and 250 rev/min. Samples of 1 ml were collected every 24 hours for monitoring various parameters of the fermentation. The composition of the inoculation and fermentation media is as described previously (Shen et al., 1986, Bio/Technology 4: 61–64).

To quantify the enzymatic degradation of the CPC, a reaction mixture was prepared, based on that described by Fujisawa et al. (1975, Agric. Biol. Chem. 39: 1303–1309) that contained, in a total volume of 100 µl: Tris-HCl, pH 8.0, 50 mM; CPC, 20 mM and culture supernatant 75 µl. The mixture was incubated for 60 minutes at 37° C. and the reaction was stopped by adding 100 µl of methanol. The proteins precipitated were removed by centrifugation for 5 minutes at 14 000 rev/min in an Eppendorff centrifuge. Production of DAC was analysed by injecting 100 µl of the reaction mixture in an HPLC Beckman System Gold equipped with a µBondapack $C_{18}$ column. Elution was performed using a mixture of solvents A (10 mM sodium acetate—acetic acid, pH 4.5) and B (100% acetonitrile) using a linear gradient from 0 to 3% of solvent B between the 0 and 2 minutes and constant 3% from minute 2 to 15 at a flow of 1.3 ml/min. The cephalosporins are detected by their absorbance at 260 nm. In these conditions DAC is eluted with a retention time of 3.1 min whereas for CPC this occurs at 8.3 min. Both compounds were identified by co-elution with standard samples of CPC and DAC.

CPC-AH activity cannot be detected until 96 h, from which moment it increases until it reaches a maximum at 168 h (FIG. 1A). Production of CPC and of DAC throughout fermentation was confirmed in the same samples, after separation by HPLC. For this, 100 µl samples were taken from the culture medium of *A. chrysogenum*, the proteins were precipitated by adding 100 µl of methanol and by centrifuging at 10 000 g for 5 minutes. 100 µl of the supernatant was analysed by HPLC in the manner described previously. Appearance of DAC in the culture media follows a course that is parallel to CPC-AH activity.

The non-specific acetylhydrolase activities present in the culture supernatants were also analysed, by testing in polyacrylamide gels (15%) developed in native conditions and staining for activity with respect to β-naphthyl acetate. To perform this test, based on that described previously by Gabriel (1971, Methods in Enzymol. 22: 578–604), the gels are loaded with 10–50 µl of culture supernatant diluted with the same quantity of buffer of native sample and are developed at 4° C. On completion of electrophoresis, the gel is immersed in a $PO_4KH_2/PO_4K_2H$ solution 50 mM pH 6.8 containing 0.05% of Fast Blue RR and 0.02% of β-naphthyl acetate. After agitation for 10 minutes, bands of a reddish colour appear, corresponding to coprecipitation of the naphthol and the Fast Blue.

The pattern of acetylhydrolases changes in the course of fermentation (FIG. 1B), no activity bands being seen up to 72 h. At 96 h, at least 4–5 bands appear, some of which disappear subsequently. Finally, at 168 h of culture, just two bands of acetylhydrolase activity are observed, which were designated CPC-AH A and CPC-AH B.

1.1.2. CPC-AH Activity of the Acetylhydrolases A and B Detected in Gels

To verify whether the acetylhydrolase activities detected in polyacrylamide gels possessed activity with respect to CPC, a preparative polyacrylamide gel was prepared and was loaded with 500 µl of culture supernatant collected at 168 hours. In one part of the gel, the presence of acetylhydrolases was determined by staining with β-naphthyl acetate and Fast Blue as described in Section 1.1.1. and, once the bands had been located, the zones of the gel that contained the upper band (A) and the lower band (B) were cut separately. As a control, to eliminate the possible effect of the acrylamide, a part of the gel in which bands of acetylhydrolase activity did not appear was also cut. The gel was soaked, 200 µl of buffer Tris-HCl 50 mM pH 8.0 was added to it and then diffusion of the enzymes from the gel to the buffer was permitted by incubation for 12 hours at 4° C. The protein extracted from band B exhibited CPC-AH activity of 14.7 pKat/mg of protein.

1.1.3. Purification of the CPC-AH B Activity

Figure 2:
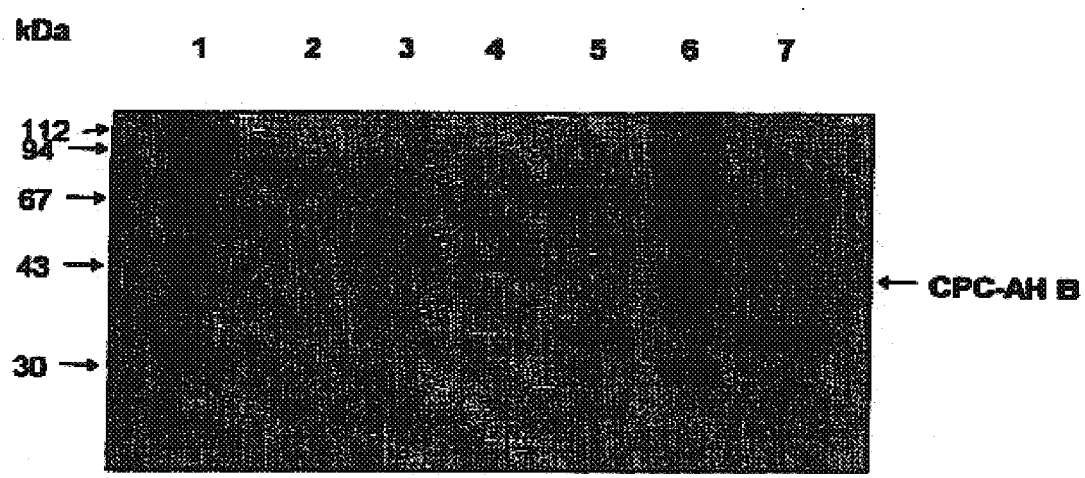
FIG. 2. SDS-PAGE analysis of the fractions obtained in the successive steps of purification of CPC-AH B activity: Lanes 1 and 6: Markers of molecular weight (the sizes of the markers in kDa are indicated by arrows on the left). 2: Culture supernatant; 3: Fraction of proteins precipitated between 30 and 60% of saturation of ammonium sulphate.

The CPC-AH B activity was purified from 2 liters of culture supernatant of *A. chrysogenum* C10 taken at 168 hours of fermentation (FIG. 2). Culture was carried out following the procedure described previously.

The proteins present in the supernatant were precipitated fractionally with increasing amounts of $(NH_4)_2SO_4$ (0–30, 30–60, 60–90% saturation) and were resuspended in buffer Tris-HCl 50 mM pH 8.0, 100 mM NaCl (buffer A). Seeing that the CPC-AH B activity appeared primarily in the protein fraction that is precipitated between 30–60% of saturation, the said fraction was loaded into a Sephadex G-75SF gel filtration column, eluted with buffer A and the acetylhydrolase activity of the fractions obtained was analysed in native polyacrylamide gels.

The fractions enriched with CPC-AH B activity were loaded into an ion exchange column DEAE-Sepharose FF equilibrated with buffer A and were eluted with a gradient of 150 ml of buffer A and 150 ml of buffer A+0.5 M NaCl. The active fractions were concentrated by ultrafiltration and 200 µl of the concentrate was loaded into a gel filtration column of FPLC Superose 12. After this process, the CPC-AH B appeared as a single band of 31 kDa in SDS-PAGE (FIG. 4).

1.2. Characterization of the Enzyme

1.2.1. Determination of Molecular Weight

The molecular weight of the CPC-AH B enzyme was determined using two techniques: (I) the molecular weight of the enzyme in its native form (not denatured) was calculated by means of gel filtration chromatography and (II) the molecular weight of the denatured protein was determined by polyacrylamide gel electrophoresis of the previously purified protein.

To estimate the molecular weight of the enzyme in the native state, a Superose 12 gel filtration column for FPLC (Pharmacia) was calibrated with proteins of known molecular weight (bovine seralbumin, 67 kDa; FGG albumin, 43 kDa; chymotrypsinogen A, 25 kDa; and ribonuclease A, 13 kDa) and then a reference straight line was constructed as a graphical representation of the $K_{AV}$ values obtained from the elution volumes of the control proteins versus the logarithms of their molecular weights.

Next, the culture supernatant of *A. chrysogenum* fermented for 168 hours in the conditions described above was collected by filtration and the proteins were precipitated with 85% saturation of $(NH_4)_2SO_4$. The precipitate was resuspended in a 20 times smaller volume of buffer A (Tris-HCl 50 mM pH 8.0) and 200 ml of this preparation was loaded in the Superose 12 column equilibrated with buffer A, eluting at a flow rate of 0.3 ml/min and collecting 0.3 ml fractions. The acetylhydrolase activities present in each fraction were analysed to determine their elution volume. With this information and knowing the total volume of the column and the dead volume, a $K_{av}$ of 0.3760 was determined for the CPC-AH B. By comparing this value with those of the calibration straight line, it was possible to calculate a molecular weight of 31 kDa for this activity (FIG. 3A).

The molecular weight of the denatured protein was determined by comparing the migration distance of the purified protein in SDS-PAGE relative to that of proteins of known molecular weight (Pharmacia) with which a calibration straight line was calculated. In these conditions the purified CPC-AH B appears as a single band of 31 kDa. This value coincides with that obtained in non-denaturing conditions and it can therefore be asserted that the active enzyme is a monomer with molecular weight of 31 kDa.

1.2.2. Determination of the Isoelectric Point

An aliquot of the previously prepared concentrated supernatant was passed through a gel filtration column of Sephadex G25 (Pharmacia) to remove the salts and was diluted in 50 ml of water Milli Q containing 10% glycerol, 4M urea and 2% ampholytes of pI 3–10. The solution thus obtained was loaded in the Rotofor preparative isoelectrofocusing apparatus (Bio-Rad). The fractions obtained after separation of the proteins according to their isoelectric point were analysed by staining of acetylhydrolase activity in polyacrylamide gels. The CPC-AH B activity appeared in the number 2 fraction of the gradient, which has a pH of 4 (FIG. 3B).

1.2.3. Effect of Substrate Concentration

With fractions obtained from ion exchange separation, tests of CPC-AH activity were performed by HPLC, varying the concentration of CPC. The activity values obtained were represented relative to the CPC concentrations (Michaelis-Menten representation), confirming their fit to a parabola. On the other hand, the inverse value of the CPC-AH B activity was represented relative to the inverse of the CPC concentration used (Lineweaver-Burk representation). Calculation by this method gave a Michaelis constant ($K_M$) of 33.72 mM and a maximum rate ($V_{max}$) of 91.95 pKat/mg (FIG. 3C).

1.2.4. Optimum Temperature and pH

To study the effect of temperature on CPC-AH B activity, tests were carried out by incubating the reaction mixtures at different temperatures (between 4 and 65° C.). The enzymatic preparation used for this was a fraction enriched with CPC-AH B obtained from anion-exchange chromatography on DEAE-Sepharose FF (Pharmacia). The CPC-AH B exhibited activity over a wide temperature range. Maximum activity was reached at 45° C. (FIG. 3D), but it is appreciable at temperatures up to 65° C. Using the aforementioned fraction, tests were performed, varying the buffer solution with which the pH is established. Potassium phosphate buffer 50 mM was employed in the range between 5 and 8, and Tris-HCl 50 mM in the range between 8 and 11. As can be seen in FIG. 3E, between pH 7 and 9 there are appreciable activity levels, reaching the maximum value of activity at pH 8. The enzyme maintains better levels of activity at alkaline pH than at acid pH.

1.2.5. Effect of Various Metals and Inhibitors

The effect of various metals and inhibitors on CPC-AH B was analysed. The enzymatic extract used for the determinations corresponded to the fractions derived from ion exchange chromatography on DEAE-Sepharose FF. These fractions were submitted to a gel filtration process in a Sephadex G-25 column (Pharmacia) to remove the residues of inorganic salts. The ions were pre-incubated for 15 minutes with the enzymatic preparations at 4° C. so that once the rest of the components of the reaction test had been added the final concentration of the ions was 1 mM. Table 1 confirms that $Mg^{2+}$, $Mn^{2+}$ and $Ca^{2+}$ have a stimulating effect, whereas $Fe^{2+}$, $Zn^{2+}$, $Ag^+$ and $Cu^{2+}$ inhibit activity to a greater or lesser extent (Table 2).

TABLE 2

Effect of various metals on CPC-AH B activity

| Metals (1 mM) | CPC-AH activity (%) |
| --- | --- |
| NONE | 100 |
| $FeSO_4$ | 49 |
| $MgSO_4$ | 141 |

TABLE 2-continued

Effect of various metals on CPC-AH B activity

| Metals (1 mM) | CPC-AH activity (%) |
|---|---|
| $MnSO_4$ | 140 |
| $CuSO_4$ | 64 |
| $ZnSO_4$ | 60 |
| $CoSO_4$ | 80 |
| $CaCl_2$ | 147 |
| NaCl | 94 |
| $K_2CO_3$ | 77 |
| $AgNO_3$ | 60 |

To determine the effect of potential inhibitors, the same extracts were used as for studying the effect of the cations, pre-incubating the extract in the same way with each compound before adding the remaining components of the reaction mixture. Among the compounds tested, attention should be drawn to the strong inhibitory effect of phenylmethylsulphonyl fluoride (PMSF) and of diisopropylfluorophosphate (DIPFPh) (Table 3).

TABLE 3

Effect of some inhibitors on CPC-AH B activity

| Inhibitors | | CPC-AH activity (%) |
|---|---|---|
| NONE | | 100 |
| EDTA | 10 mM | 86 |
| | 1 mM | 87 |
| | 0.1 mM | 91 |
| PMSF | 10 mM | 0 |
| | 1 mM | 11 |
| | 0.1 mM | 59 |
| | 0.01 mM | 91 |
| DIPFPh | 10 mM | 0 |
| | 0 mM | 9 |
| | 0.1 mM | 7 |

1.2.6. Sequencing the Amino Terminus of CPC-AH B

To determine the amino acid sequence of the amino terminus of CPC-AH B, 100 pmol of the purified protein was loaded in a 15% SDS-PAGE gel and transferred to a PVDF membrane (Immobilon P, Millipore) using the MiniTrans-Blot system (BioRad). The transfer buffer used was CAPS 10 mM pH 11.0 with 10% methanol. The zone of the filter that contained the electrophoresis band of protein corresponding to CPC-AH B activity was cut and was submitted to 21 cycles of Edman degradation in an automatic protein sequencer 476A (Applied Biosystems) following the manufacturer's instructions. The amino acid sequence is shown in SEQ ID NO 1.

EXAMPLE 2

2.1. Cloning of the cahB Gene

As a function of the amino terminal sequence of the CPC-AH B enzyme and by using the standard for use of codons of genes of *A. chrysogenum*, a synthetic oligonucleotide was designed corresponding to the preceding 5' end of the gene. The sequence of this oligonucleotide is shown in SEQ ID NO 2.

After analysis of this sequence, it was confirmed that it is similar to the amino acid sequence of protease T of the fungus *T. album* (Samal et al., 1989, Mol. Microbiol. 4: 1789–1792) whose corresponding gene had already been cloned and sequenced. Comparison of this sequence with that of other known proteases revealed the existence of fully conserved zones in all of them. One of these zones, concretely that corresponding to the active centre (Pro-His-Val-Ala-Gly-Leu), was employed for elaborating the oligonucleotide described in SEQ ID NO 3, which enabled us to perform PCR reactions together with the oligonucleotide described in SEQ ID NO 2.

Cloning of the gene corresponding to the protein CPC-AH B was attempted by screening a gene library of the strain *A. chrysogenum* C10 previously effected in the λEMBL3-ble substitution vector (Gutiérrez et al. 1991, J. Bacteriol. 173: 1354–2365) with two probes with different origin: Probe 1: 1020 pb fragment EcoRI-DraI corresponding to the gene that codes for protease T of *T. album*. Probe 2: 700 pb fragment obtained by PCR, using the oligonucleotides described in SEQ ID NO 2 and SEQ ID NO 3 and, as pattern, total DNA of *A. chrysogenum* C10.

The positive phages were purified and characterized by Southern analysis in accordance with standard techniques (Sambrook et al. 1989, Molecular Cloning: A Laboratory Manual, Cold Spring Harbor Laboratory, Cold Spring Harbor, N.Y., USA). As a result of the series of cycles of hybridization and purification we obtained phage F41, which contained the cahB gene (FIG. 4A).

In EcoRI digestion of phage F41, a 5 kb hybridization band appeared, which was regarded as suitable for its subcloning, mapping and sequencing (FIG. 4B). The said 5 kb fragment EcoRI was subcloned in pBluescript I KS(+) (Stratagene) in its two orientations and was mapped with various restriction enzymes. The agarose gel resulting from the mapping was transferred to a nylon filter and was hybridized with the aforementioned probe 1, obtaining positive signals. Among them, we determined the existence of a DNA fragment SmaI-EcoRI of approximately 1.6 kb, which was large enough to contain the complete gene since the expected size was approximately 1.2 kb. Therefore the fragment SmaI-EcoRI was subcloned (after generating flush ends with Klenow) at the SmaI site in pBluescript I KS(+) in the two orientations. The two plasmids obtained were designated pJE11A and pJE11B.

2.2. Nucleotide Sequence of the cahB Gene

The pJE11A and pJE11B plasmids were digested with BstXI and XbaI so that they could then be submitted to a process of unidirectional deletions using the erase-a-base kit (Promega) in accordance with the manufacturer's instructions. A total of 8 clones of each orientation were selected, and these were sequenced using the usual methods. In this way a sequence of 1621 pb was obtained, corresponding to the whole of the fragment SmaI-EcoRI (SEQ ID NO 4). In this sequence we detected an open reading frame (ORF) of 383 amino acids, interrupted by two introns of 68 and 78 pb, in which we determined the presence of consensus processing sequences situated at 5', 3' and internally, conserved in the introns of fungi.

The polypeptide deduced can be seen in the three-letter amino acid code, under its corresponding triplets in SEQ ID NO: 4 and also in an isolated context in SEQ ID NO: 5. A series of searches made in the protein database (SwissProt) of the public access server BLAST of the National Centre for Biotechnology Information (NCBI, USA) revealed that the amino acid sequence has similarity with proteases produced by the fungus *T. album* with which it displayed the following identity (Table 1): 64.5% with preprotease T, 49.5% of identity with preendoprotease K and 48.5% with preprotease R. Therefore the sequence of the cahB gene shows that the enzyme is strongly related to alkaline proteases of fungal origin. The active centre of various esterases and lipases shows a high degree of similarity with that of b-lactamases and proteases (Cygler et al. 1993 Protein Science 2: 366–382). CPC-AH B is more related to serine proteases of the subtilase type (Siezen et al. 1991, Protein Eng. 4: 719–737). The active centre of these enzymes is formed by the so-called catalytic triad (aspartic acid, serine and histidine). The typical amino acids of the said active centre have been located in the sequence of CPC-AH B at positions $D^{145}$, $H^{176}$ and $S^{331}$, respectively. Moreover, a high degree of conservation can be observed in the amino acids close to those that form this triad in the 4 enzymes compared.

The amino acid sequence deduced from sequencing of the purified CPC-AH B coincides exactly with that of amino acids 107 to 127 of the protein deduced from the gene. This indicates that *A. chrysogenum* first synthesizes a preprotein of 383 amino acids that is processed between positions $Gln^{106}$ and $Ala^{107}$ to form the mature protein of 277 amino acids (SEQ ID NO: 6). The molecular weight (26.9 kDa) and the pI (3.5) deduced from the DNA sequence of the mature protein differ slightly from those deduced experimentally. These differences may be due to post-translational glycoxylations or irregular electrophoretic migration of the protein.

2.3. Analysis of Transcription of the cahB Gene

With the aim of studying the temporal pattern of transcription of the cahB gene, a Northern analysis was carried out in accordance with standard techniques (Sambrook et al. 1989, Molecular Cloning: A Laboratory Manual, Cold Spring Harbor Laboratory, Cold Spring Harbor, N.Y., USA) starting from total RNA extracted by methods described previously (Ausubel et al. 1987, Current Protocols in Molecular Biology. Wiley, New York) from mycelium samples taken every 24 hours from inoculation up to 120 hours of fermentation (FIG. 5). The RNA samples were hybridized with a DNA probe SmaI-EcoRI of 1.6 kb that includes the cahB gene. The same RNA preparations were hybridized with a probe KpnI-NcoI of 0.83 kb internal to the gene of β-actin of *Aspergillus nidulans*. This hybridization was used as control of the quantity and quality of the RNA since transcription of the gene of β-actin does not vary in the course of fermentation.

The Northern analysis showed that the cahB gene is transcribed forming a single messenger RNA of about 1.4 kb. This transcript was only detected at 72 and 96 hours, but could not be detected in earlier and later samples. According to these results, there seems to be a delay of approximately 24 hours between the moment of transcription (72 hours) and the moment when the CPC-AH B protein appears in the fermentation media (96 hours). This delay may be due to the time required for translation, processing and transport of the protein to the culture medium.

2.4. Chromosomal Localization of the cahB Gene

The DNA samples for separating whole chromosomes by the PFGE technique (pulsed-field gel electrophoresis) have to be prepared by a method that releases the DNA from the other cellular components of the fungus without causing physical rupture or enzymatic degradation. For this purpose, a protocol was applied that consisted of obtaining protoplasts from the mycelium of the fungus followed by enzymatic and chemical treatment of the said protoplasts to obtain the DNA, free and intact. The protoplasts were prepared according to a method described previously (Gutiérrez et al. 1991, Mol. Gen. Genet. 225: 56–64).

Resolution of the chromosomes was effected in a CHEF-DRII system (BioRad). The gel was prepared with agarose of chromosomal grade (BioRad) at 0.6%. The electrophoresis buffer was Tris 0.05 M, boric acid 0.05 M and NaEDTA 0.1 mM. Electrophoresis was carried out for 216 hours at 40 V with the buffer at a temperature of 9° C., replacing it with fresh buffer every 72 hours. Using this technique, seven chromosome bands of the genome of *A. chrysogenum* were separated. By comparison with the chromosomes of *A. nidulans, Schyzosaccharomyces pombe* and *Saccharomyces cerevisiae*, sizes of 5.3, 4.6, 4.1, 3.8, 2.8, 2.4 and 2.2 Mb were estimated for the seven bands of *A. chrysogenum*. The 3.8 Mb band displayed greater intensity suggesting the presence of two chromosomes of similar size. The chromosomes were numbered from I to VIII in increasing order of size.

The cahB gene was located by hybridization in the larger chromosome (5.3 Mb). The autoradiograph (FIG. 6) shows two additional signals corresponding to DNA retained in the gel dish and to DNA degraded in the lower part of the gel.

EXAMPLE 3

3.1. Cloning of the cahB Gene Starting from a cDNA Library

With the aim of obtaining the CPC-AH B protein in large quantity, expression of the cahB gene in *Escherichia coli* was considered. This prokaryotic system permits efficient expression of the heterologous proteins when the coding region of the gene is located under start signals of transcription and translation that are well recognized by the bacterium. However, eukaryotic genes can be interrupted by introns which are not processed by the prokaryotes, therefore necessitating prior cloning of the gene of interest starting from a cDNA library. For this purpose, a cDNA library was constructed starting from RNA of the strain *A. chrysogenum* C10 using the ZAP-cDNA system (Stratagene) following the manufacturer's instructions.

The cahB gene in the form of cDNA was isolated from this library by methods already described (Sambrook et al. 1989, Molecular Cloning: A Laboratory Manual, Cold Spring Harbor Laboratory, Cold Spring Harbor, N.Y., USA) using as probe a 715 bp fragment of DNA internal to the cahB gene. As a result of this screening, four positive clones were obtained, and from one of these we purified a 567 bp fragment internal to the cahB gene but lacking introns. This fragment is the cDNA sequence corresponding to SEQ ID NO:4.

3.2. Expression in *Escherichia coli*

The 715 pb genomic fragment (BamHI-NcoI) of the pJE11A plasmid was replaced by the 567 pb fragment with the same termini, giving as a result the plasmid pJEB12, which contained the cahB gene without introns (FIG. 7). Final construction for its expression in *E. coli* was effected with a 1257 pb fragment obtained by PCR, using the oligonucleotides SEQ ID NO: 7 and SEQ ID NO: 8 and as pattern pJE12. The 1155 pb fragment was treated with Klenow, digested with SalI and subcloned in the pT7.7 plasmid (NdeI, Klenow, SalI) giving as a result the plasmid pT7B2.1. Similarly, but using the oligonucleotides SEQ ID NO: 9 and SEQ ID NO: 8, an 839 pb fragment was prepared by PCR that corresponded to the processed protein lacking the first 106 amino acids of the preprotein. The plasmid generated by ligation of this fragment filled with klenow and digested with SalI in pT7.7 (NdeI, Klenow, SalI) was designated pT7B2.2.

The plasmids pTB2.1 and pTB2.2 were transformed in *E. coli* JM109(DE3) and the transformants were grown in LB medium on adding 100 μg/ml of ampicillin (LB-Ap) at 37° C. for 12 hours. 100 ml of fresh LB-Ap medium was inoculated with 2 ml of the previous culture and was incubated at 37° C. and 250 rev/min until the culture reached an OD at 600 nm of 0.4 units. At this moment IPTG was added to a final concentration of 0.5 mM and the cells were collected by centrifugation 3 hours later. Synthesis of heterologous proteins was analysed by SDS-PAGE. In extracts of the *E. coli* strain JM109(DE3) transformed with the pT7B2.1. plasmid, a protein band of 42 kDa appeared, corresponding to the CPC-AH B enzyme without processing, whereas the extracts from the transformant with the pT7B2.2. plasmid had a 31 kDa band corresponding to the processed CPC-AH B (FIG. 8). In the transformants of *E. coli* JM109(DE3)/pT7B2.2, weak CPC-AH activity was detected, whereas this enzymatic activity did not appear in those of *E. coli* JM109(DE3)/pT7B2.1.

EXAMPLE 4
4.1. Deacetylation of CPC and Derivatives

Enzymatic extracts obtained from *E. coli* JM109(DE3)/pT7B2.2 were used for in-vitro deacetylation both of CPC and of 7-ACA in the same conditions as described in Section 1.1.1 (Example 1) for the determination of CPC-AH activities in *A. chrysogenum*. In the reaction of deacetylation of 7-ACA the CPC was replaced by 7-ACA at a concentration of 20 mM. In both cases we detected appearance of the corresponding deacetylated derivatives: deacetyl CPC (DAC) and deacetyl 7-ACA.

EXAMPLE 5
5.1. Inactivation of the cahB Gene in *A. chrysogenum*

For the purpose of inactivating the CPC-AH B activity we employed the technique of gene disruption by simple integration. In this process we attempt to generate two mutated copies of the gene, which is achieved when recombination occurs between an internal fragment of the target gene, located in a plasmid, and the endogenous target gene. In our case, the cahB gene is relatively small (1.1 kb) and recombination in *A. chrysogenum* is described as being primarily by a heterologous route. To promote homologous recombination, a genomic DNA fragment of 7 kb that contained the cahB gene was employed for constructing the plasmid.

For the two copies of the mutated target gene to be generated, it is necessary to introduce two mutations in the gene and recombination has to take place between these two points. For this, two mutations were generated at the 5' end of the cahB gene by eliminating the BamHI and KpnI restriction sites in each. The KpnI restriction site was eliminated using the Quickchange kit (Stratagene) following the manufacturer's instructions. At the 3' end of the gene, a mutation was introduced in the StyI restriction site.

The 7 kb fragment with the 3 mutations mentioned above was introduced into the pJL43 plasmid, giving rise to the plasmid pB*2 (FIG. 9). Prior to the transformation, the pB*2 plasmid was digested with ClaI (which is located between the two mutations introduced into the gene) to generate a linear molecule, as it has been described that transformation with linear plasmids promotes recombination. *A. chrysogenum* C10 was transformed with these plasmids following the method described by Gutiérrez et al. (1991, Mol. Gen. Genet. 225: 56–64). The transformants were selected in TSA medium supplemented with saccharose (10.3%) and phleomycin (40 μg/ml).

5.2. Increase in Yield of Cephalosporin in the Transformants of *A. chrysogenum* with the Inactivated cahB Gene The yield of cephalosporin from the two transformants was determined every 24 hours in samples obtained from fermentation in the conditions described previously. The presence of acetylhydrolase activities in the culture media was analysed using native polyacrylamide gels in the samples taken at 168 hours. At least 3 out of 10 transformants analysed (C1A, C3A and C5A) lacked CPC-AH B activity (FIG. 10). In another gel, loaded with the same samples but stained with Coomassie blue for detecting the presence of total proteins, absence of the protein band associated with CPC-AH B activity was confirmed in transformants C1A, C3A and C5A.

Among the transformants with the supposedly inactivated cahB gene, C3A was chosen for verifying whether absence of CPC-AH B activity is maintained throughout fermentation. For this, we analysed the supernatants collected every 24 hours both from this transformant and from the strain *A. chrysogenum* C10 without transformation. The band of CPC-AH B activity did not appear in any of the samples from the C3A transformant that were analysed, whereas the pattern of the remaining acetylhydrolase activities remained similar to those of the control strain C10 (FIGS. 11A and 11B). Absence of CPC-AH B activity in the C3A transformant showed up as a change in the proportion of DAC and CPC in the culture media collected at 168 hours and analysed by HPLC. In the chromatograms (FIG. 12) it was observed that the concentration of CPC is greater (32%) in the transformant with the inactivated enzyme than in the strain *A. chrysogenum* C10 without transformation, whereas the concentration of DAC decreased appreciably (41%) in the transformant.

What is claimed is:

1. An isolated DNA sequence comprising SEQ ID NO:4 or a fragment of SEQ ID NO:4 encoding a peptide with cephalosporin C(CPC)-acetylhydrolase enzymatic activity.

2. The DNA sequence according to claim 1, wherein the sequence comprises SEQ ID NO:4.

3. The DNA sequence according to claim 1, wherein the sequence encodes the polypeptide of SEQ ID NO:5.

4. The DNA sequence according to claim 1, wherein the DNA sequence encodes the polypeptide of SEQ ID NO:6.

5. A vector comprising the DNA sequence of claim 1.

6. The vector of claim 5, wherein the vector is a plasmid.

7. A vector comprising the DNA sequence of claim 2.

8. The vector of claim 7, wherein the vector is a plasmid.

9. A microorganism transformed with the vector of claim 5.

10. The transformed microorganism of claim 9, wherein the microorganism is *E coli*.

11. A microorganism transformed with the vector of claim 7.

12. The microorganism of claim 11, wherein the microorganism is *E. coli*.

13. A method of expressing CPC-acetylhydrolase activity comprising:
   (a) providing a microorganism that is susceptible to transformation with the isolated DNA sequence of claim 1 and that, upon transformation, expresses the CPC-acetylhydrolase activity encoded by said DNA sequence; and
   (b) transforming the microorganism with the isolated DNA sequence to cause expression of the CPC-acetylhydrolase activity in the microorganism.

14. The method according to claim 13, wherein the method further comprises using the expressed CPC-acetylhydrolase activity to prepare a deacetylated derivative of cephalosporin C or 7-aminocephalosporanic acid.

15. The method according to claim 14, wherein the derivative is deacetylcephalosporin C or deacetyl 7-aminocephalosporanic acid.

16. A method of expressing CPC-acetylhydrolase activity comprising:
   (a) providing a microorganism that is susceptible to transformation with the isolated DNA sequence of claim 3 and that, upon transformation, expresses the CPC-acetylhydrolase activity encoded by said DNA sequence; and
   (b) transforming the microorganism with the DNA sequence to cause expression of the CPC-acetylhydrolase activity in the microorganism.

17. The method according to claim 16, wherein the method further comprises using the expressed CPC-acetylhydrolase activity to prepare a deacetylated derivative of cephalosporin C or 7-aminocephalosporanic acid.

18. The method according to claim 17, wherein the derivative is deacetylcephalosporin C or deacetyl 7-aminocephalosporanic acid.

19. A method of expressing CPC-acetylhydrolase activity comprising:
   (a) providing a microorganism that is susceptible to transformation with the isolated DNA sequence of claim 4 and that, upon transformation, expresses the CPC-acetylhydrolase activity encoded by said DNA sequence; and
   (b) transforming the microorganism with the DNA sequence to cause expression of the CPC-acetylhydrolase activity in the microorganism.

20. The method according to claim 19, wherein the method further comprises using the expressed CPC-acetylhydrolase activity to prepare a deacetylated derivative of cephalosporin C or 7-aminocephalosporanic acid.

21. The method according to claim 20, wherein the derivative is deacetylcephalosporin C or deacetyl 7-aminocephalosporanic acid.

* * * * *

UNITED STATES PATENT AND TRADEMARK OFFICE
CERTIFICATE OF CORRECTION

PATENT NO. : 6,815,189 B1
DATED : November 9, 2004
INVENTOR(S) : Javier Velasco Alvarez et al.

It is certified that error appears in the above-identified patent and that said Letters Patent is hereby corrected as shown below:

Title page,
Item [73], Assignee, "Antibiotics" should read -- Antibioticos --.

Signed and Sealed this

Twenty-fifth Day of January, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 21
<212> TYPE: PRT
<213> ORGANISM: Acremonium chrysogenum
<220> FEATURE:
<223> OTHER INFORMATION: Amino acid sequence corresponding to the amino
      terminus of the CPC-AH B enzyme of Acremonium
      chrysogenum

<400> SEQUENCE: 1

Ala Thr Gln Glu Asn Ala Pro Trp Gly Leu Ala Arg Ile Ser Ser Gln
 1               5                  10                  15

```
                                 -continued
Glu Pro Gly Gly Ser
             20

<210> SEQ ID NO 2
<211> LENGTH: 36
<212> TYPE: DNA
<213> ORGANISM: Tritirachium album
<220> FEATURE:
<223> OTHER INFORMATION: Synthetic oligonucleotide deduced starting from
      the amino acid sequence of the amino terminus of
      the CPC-AH B of Acremonium chrysogenum

<400> SEQUENCE: 2
gccacccagg agaacgcccc ctggggcctc gcccgc                              36

<210> SEQ ID NO 3
<211> LENGTH: 18
<212> TYPE: DNA
<213> ORGANISM: Tritirachium album
<220> FEATURE:
<223> OTHER INFORMATION: Synthetic oligonucleotide deduced starting from
      the amino acid sequence (Pro-His-Val-Ala-Gly-Leu)
      of the active centre of protease T of Tritirachium
      album

<400> SEQUENCE: 3
gaggccggcg acgtgggg                                                  18

<210> SEQ ID NO 4
<211> LENGTH: 1621
<212> TYPE: DNA
<213> ORGANISM: Acremonium chrysogenum
<220> FEATURE:
<221> NAME/KEY: CDS
<222> LOCATION: (162)..(620)
<223> OTHER INFORMATION: DNA sequence derived from Acremonium
      chrysogenum corresponding to the cahB gene
<223> OTHER INFORMATION: Immediate experimental source of the sequence:
      plasmid pJE11B
<223> OTHER INFORMATION: Position of the sequence in the genome:
      Chromosome VIII
<221> NAME/KEY: mat_peptide
<222> LOCATION: (480)
<221> NAME/KEY: CDS
<222> LOCATION: (689)..(862)
<221> NAME/KEY: CDS
<222> LOCATION: (941)..(1456)

<400> SEQUENCE: 4
cccgggcctt gtaatcaatg ccatgagtcg catcgaggag gataaataga tgagttccgc   60
acctcccagt gctcttctcc ttccctccat cccatcccaa cccatcatca accacccatc  120
catccaacca aactaccctt ccttgatcca ataccgccat c atg cgt gct gct act  176
                                             Met Arg Ala Ala Thr
                                                            -105 ctc ctc gct ctc gtc ccc cta gcg ctg gcc gct cct tcc gcc gtg aaa   224
Leu Leu Ala Leu Val Pro Leu Ala Leu Ala Ala Pro Ser Ala Val Lys
    -100                 -95                 -90 cgc gat gct ccg gct ccc gtc ctt gct ccc cgc gac gcc aag ctc gtc   272
Arg Asp Ala Pro Ala Pro Val Leu Ala Pro Arg Asp Ala Lys Leu Val
-85                 -80                 -75                 -70 ccc ggc aag tac atc gtc aag ttc aag aag gac tcc gtc tca acc gcc   320
Pro Gly Lys Tyr Ile Val Lys Phe Lys Lys Asp Ser Val Ser Thr Ala
                -65                 -60                 -55 gtc tcc tcg gcc atc cag agc att gct gcc tct gcc gac tac acc tac   368
Val Ser Ser Ala Ile Gln Ser Ile Ala Ala Ser Ala Asp Tyr Thr Tyr
            -50                 -45                 -40
```

-continued

| | |
|---|---|
| gcg aag cac ttc aac ggt ttc gcc gcc agc ctc act gat gct gag atc<br>Ala Lys His Phe Asn Gly Phe Ala Ala Ser Leu Thr Asp Ala Glu Ile<br>     -35               -30                       -25 | 416 |
| aag aag ctg agg gac gac ccc aac gtc gag tac att gag cag gac gcc<br>Lys Lys Leu Arg Asp Asp Pro Asn Val Glu Tyr Ile Glu Gln Asp Ala<br>     -20               -15                     -10 | 464 |
| att gtc act atc cag gcc act cag gag aac gcc ccc tgg ggt ctt gcc<br>Ile Val Thr Ile Gln Ala Thr Gln Glu Asn Ala Pro Trp Gly Leu Ala<br>    -5               -1   1            5                   10 | 512 |
| cgc atc tcc agc cag gag ccc ggc ggc agc acc tac acc tat gat gat<br>Arg Ile Ser Ser Gln Glu Pro Gly Gly Ser Thr Tyr Thr Tyr Asp Asp<br>               15                 20                 25 | 560 |
| tct gcc ggt gct ggt acc tgc tct tgg atc ctc gac acc ggt atc gat<br>Ser Ala Gly Ala Gly Thr Cys Ser Trp Ile Leu Asp Thr Gly Ile Asp<br>         30                 35                40 | 608 |
| acc gac cac cct gtatgtggcc ttcccttacc cataccctcat tcccaacgtc<br>Thr Asp His Pro<br>        45 | 660 |
| gcagaaatat cgaactaact gattgtag gac ttc ggt ggc cgt gcc tcc ttt<br>                                         Asp Phe Gly Gly Arg Ala Ser Phe<br>                                                  50                       55 | 712 |
| gcc gcc aac ttc gct gac gag aat gac tcc gat gtt cag ggg cat ggc<br>Ala Ala Asn Phe Ala Asp Glu Asn Asp Ser Asp Val Gln Gly His Gly<br>               60                       65                      70 | 760 |
| act cac gtt gct ggc act gtt ggc ggc tct acc tac ggt gtg gct aag<br>Thr His Val Ala Gly Thr Val Gly Gly Ser Thr Tyr Gly Val Ala Lys<br>             75                      80                    85 | 808 |
| gag act aag ctg ttc gcc gtt aag gtc ctc ggc gac gac ggt agc ggt<br>Glu Thr Lys Leu Phe Ala Val Lys Val Leu Gly Asp Asp Gly Ser Gly<br>         90                     95                   100 | 856 |
| act aag tgagtttggc cttttacacg cttctccgtg ttttcccaac tcgagttttg<br>Thr Lys<br>105 | 912 |
| atagctaacg atgggtacct gtaacagc gct ggt gtc atc gct ggt atg gag<br>                                        Ala Gly Val Ile Ala Gly Met Glu<br>                                                               110 | 964 |
| tac gtt gcg gac aat gcc ggc tct gag gac tgc ccc aac ggc tcc gtc<br>Tyr Val Ala Asp Asn Ala Gly Ser Glu Asp Cys Pro Asn Gly Ser Val<br>     115                 120                 125 | 1012 |
| gcc aac atg tcc ctg ggc ggt ggc ttc tcc agc gcc atc aac gat ccc<br>Ala Asn Met Ser Leu Gly Gly Gly Phe Ser Ser Ala Ile Asn Asp Pro<br>130                 135                 140                 145 | 1060 |
| gcc gac gct atc gtg agc gcc ggc atc ttc ctc gct gtc gcc gct ggc<br>Ala Asp Ala Ile Val Ser Ala Gly Ile Phe Leu Ala Val Ala Ala Gly<br>                 150                 155                 160 | 1108 |
| aat gac ggt gct gat gct gcc gac ttc tcc ccc gca tct gcc ccc tcg<br>Asn Asp Gly Ala Asp Ala Ala Asp Phe Ser Pro Ala Ser Ala Pro Ser<br>               165                 170                 175 | 1156 |
| gcc tgc act gtc ggt gcc act acc tct agc gac ggc ctc gcc tcc ttc<br>Ala Cys Thr Val Gly Ala Thr Thr Ser Ser Asp Gly Leu Ala Ser Phe<br>         180                 185                 190 | 1204 |
| tcc aac tgg ggc agc atc gtc gat gtt ctt gcc ccc ggc cag gat gtt<br>Ser Asn Trp Gly Ser Ile Val Asp Val Leu Ala Pro Gly Gln Asp Val<br>     195                 200                 205 | 1252 |
| ctc tct tcc atc ccc ggc ggt ggc gag gac tcc ctc tcc gga act tcc<br>Leu Ser Ser Ile Pro Gly Gly Gly Glu Asp Ser Leu Ser Gly Thr Ser<br>210                 215                 220                 225 | 1300 |
| atg gcc tcc cct cat gtg gcc ggt ctt gcc gcc tac ctg atg ggc acc<br>Met Ala Ser Pro His Val Ala Gly Leu Ala Ala Tyr Leu Met Gly Thr<br>               230                 235                 240 | 1348 |

```
ggt gcc agc gtc agc ggt ctc tgc gac act att gcc tcc tcg gca ctc       1396
Gly Ala Ser Val Ser Gly Leu Cys Asp Thr Ile Ala Ser Ser Ala Leu
            245                 250                 255 gag ggt gtc atc tcc ggc gtc ccc agc gac acc gcc aac ctt ctc atc       1444
Glu Gly Val Ile Ser Gly Val Pro Ser Asp Thr Ala Asn Leu Leu Ile
            260                 265                 270 aac aac ggc cag taaatggtta acgagcatg gggtgtccgc cctgtcgata            1496
Asn Asn Gly Gln
        275 cccggcagcc tcgtgagcta gcgcgatggc cagtgtggaa tgggacggat gatggaactg    1556 gttgatggat gcatgtgagg acgtggaccg ccgccactcc tcaccccyg catggatggg    1616 aattc                                                                  1621

<210> SEQ ID NO 5
<211> LENGTH: 383
<212> TYPE: PRT
<213> ORGANISM: Acremonium chrysogenum

<400> SEQUENCE: 5

Met Arg Ala Ala Thr Leu Leu Ala Leu Val Pro Leu Ala Leu Ala Ala
    -105                -100                -95

Pro Ser Ala Val Lys Arg Asp Ala Pro Ala Pro Val Leu Ala Pro Arg
-90                 -85                 -80                 -75

Asp Ala Lys Leu Val Pro Gly Lys Tyr Ile Val Lys Phe Lys Lys Asp
                -70                 -65                 -60

Ser Val Ser Thr Ala Val Ser Ser Ala Ile Gln Ser Ile Ala Ala Ser
                -55                 -50                 -45

Ala Asp Tyr Thr Tyr Ala Lys His Phe Asn Gly Phe Ala Ala Ser Leu
            -40                 -35                 -30

Thr Asp Ala Glu Ile Lys Lys Leu Arg Asp Asp Pro Asn Val Glu Tyr
        -25                 -20                 -15

Ile Glu Gln Asp Ala Ile Val Thr Ile Gln Ala Thr Gln Glu Asn Ala
-10                 -5                  -1   1                  5

Pro Trp Gly Leu Ala Arg Ile Ser Ser Gln Glu Pro Gly Gly Ser Thr
                10                  15                  20

Tyr Thr Tyr Asp Asp Ser Ala Gly Ala Gly Thr Cys Ser Trp Ile Leu
                25                  30                  35

Asp Thr Gly Ile Asp Thr Asp His Pro Asp Phe Gly Gly Arg Ala Ser
        40                  45                  50

Phe Ala Ala Asn Phe Ala Asp Glu Asn Asp Ser Asp Val Gln Gly His
55                  60                  65                  70

Gly Thr His Val Ala Gly Thr Val Gly Ser Thr Tyr Gly Val Ala
                75                  80                  85

Lys Glu Thr Lys Leu Phe Ala Val Lys Val Leu Gly Asp Asp Gly Ser
                90                  95                  100

Gly Thr Lys Ala Gly Val Ile Ala Gly Met Glu Tyr Val Ala Asp Asn
            105                 110                 115

Ala Gly Ser Glu Asp Cys Pro Asn Gly Ser Val Ala Asn Met Ser Leu
        120                 125                 130

Gly Gly Gly Phe Ser Ser Ala Ile Asn Asp Pro Ala Asp Ala Ile Val
135                 140                 145                 150

Ser Ala Gly Ile Phe Leu Ala Val Ala Ala Gly Asn Asp Gly Ala Asp
                155                 160                 165

Ala Ala Asp Phe Ser Pro Ala Ser Ala Pro Ser Ala Cys Thr Val Gly
```

```
                       170                 175                 180
Ala Thr Thr Ser Ser Asp Gly Leu Ala Ser Phe Ser Asn Trp Gly Ser
                185                 190                 195
Ile Val Asp Val Leu Ala Pro Gly Gln Asp Val Leu Ser Ser Ile Pro
            200                 205                 210
Gly Gly Gly Glu Asp Ser Leu Ser Gly Thr Ser Met Ala Ser Pro His
215                 220                 225                 230
Val Ala Gly Leu Ala Ala Tyr Leu Met Gly Thr Gly Ala Ser Val Ser
                235                 240                 245
Gly Leu Cys Asp Thr Ile Ala Ser Ser Ala Leu Glu Gly Val Ile Ser
            250                 255                 260
Gly Val Pro Ser Asp Thr Ala Asn Leu Leu Ile Asn Asn Gly Gln
                265                 270                 275

<210> SEQ ID NO 6
<211> LENGTH: 153
<212> TYPE: PRT
<213> ORGANISM: Acremonium chrysogenum

<400> SEQUENCE: 6

Met Arg Ala Ala Thr Leu Leu Ala Leu Val Pro Leu Ala Leu Ala Ala
  1               5                  10                  15
Pro Ser Ala Val Lys Arg Asp Ala Pro Ala Pro Val Leu Ala Pro Arg
                 20                  25                  30
Asp Ala Lys Leu Val Pro Gly Lys Tyr Ile Val Lys Phe Lys Lys Asp
             35                  40                  45
Ser Val Ser Thr Ala Val Ser Ser Ala Ile Gln Ser Ile Ala Ala Ser
         50                  55                  60
Ala Asp Tyr Thr Tyr Ala Lys His Phe Asn Gly Phe Ala Ala Ser Leu
 65                  70                  75                  80
Thr Asp Ala Glu Ile Lys Lys Leu Arg Asp Asp Pro Asn Val Glu Tyr
                 85                  90                  95
Ile Glu Gln Asp Ala Ile Val Thr Ile Gln Ala Thr Gln Glu Asn Ala
                100                 105                 110
Pro Trp Gly Leu Ala Arg Ile Ser Ser Gln Glu Pro Gly Gly Ser Thr
            115                 120                 125
Tyr Thr Tyr Asp Asp Ser Ala Gly Ala Gly Thr Cys Ser Trp Ile Leu
        130                 135                 140
Asp Thr Gly Ile Asp Thr Asp His Pro
145                 150

<210> SEQ ID NO 7
<211> LENGTH: 58
<212> TYPE: PRT
<213> ORGANISM: Acremonium chrysogenum

<400> SEQUENCE: 7

Asp Phe Gly Gly Arg Ala Ser Phe Ala Ala Asn Phe Ala Asp Glu Asn
  1               5                  10                  15
Asp Ser Asp Val Gln Gly His Gly Thr His Val Ala Gly Thr Val Gly
                 20                  25                  30
Gly Ser Thr Tyr Gly Val Ala Lys Glu Thr Lys Leu Phe Ala Val Lys
             35                  40                  45
Val Leu Gly Asp Asp Gly Ser Gly Thr Lys
         50                  55
```

```
<210> SEQ ID NO 8
<211> LENGTH: 172
<212> TYPE: PRT
<213> ORGANISM: Acremonium chrysogenum

<400> SEQUENCE: 8

Ala Gly Val Ile Ala Gly Met Glu Tyr Val Ala Asp Asn Ala Gly Ser
 1               5                  10                  15

Glu Asp Cys Pro Asn Gly Ser Val Ala Asn Met Ser Leu Gly Gly Gly
            20                  25                  30

Phe Ser Ser Ala Ile Asn Asp Pro Ala Asp Ala Ile Val Ser Ala Gly
        35                  40                  45

Ile Phe Leu Ala Val Ala Ala Gly Asn Asp Gly Ala Asp Ala Ala Asp
 50                  55                  60

Phe Ser Pro Ala Ser Ala Pro Ser Ala Cys Thr Val Gly Ala Thr Thr
 65                  70                  75                  80

Ser Ser Asp Gly Leu Ala Ser Phe Ser Asn Trp Gly Ser Ile Val Asp
                85                  90                  95

Val Leu Ala Pro Gly Gln Asp Val Leu Ser Ser Ile Pro Gly Gly Gly
            100                 105                 110

Glu Asp Ser Leu Ser Gly Thr Ser Met Ala Ser Pro His Val Ala Gly
        115                 120                 125

Leu Ala Ala Tyr Leu Met Gly Thr Gly Ala Ser Val Ser Gly Leu Cys
130                 135                 140

Asp Thr Ile Ala Ser Ser Ala Leu Glu Gly Val Ile Ser Gly Val Pro
145                 150                 155                 160

Ser Asp Thr Ala Asn Leu Leu Ile Asn Asn Gly Gln
                165                 170

<210> SEQ ID NO 9
<211> LENGTH: 20
<212> TYPE: DNA
<213> ORGANISM: Acremonium chrysogenum
<220> FEATURE:
<223> OTHER INFORMATION: Synthetic oligonucleotide corresponding to the
      5' end of the cahB gene of Acremonium chrysogenum

<400> SEQUENCE: 9
tgcgtgctgc tactctcctc                                                    20

<210> SEQ ID NO 10
<211> LENGTH: 27
<212> TYPE: DNA
<213> ORGANISM: Acremonium chrysogenum
<220> FEATURE:
<223> OTHER INFORMATION: Synthetic oligonucleotide complementary to the
      3' terminus of the cahB gene of Acremonium chrysogenum

<400> SEQUENCE: 10
tttgtcgact tactggccgt tgttgat                                            27

<210> SEQ ID NO 11
<211> LENGTH: 23
<212> TYPE: DNA
<213> ORGANISM: Acremonium chrysogenum
<220> FEATURE:
```

-continued

<223> OTHER INFORMATION: Synthetic oligonucleotide corresponding to the
      region of the cahB gene of Acremonium chrysogenum
      that codes for the processed protein (without the
      first 106 amino acids of the preprotein).

<400> SEQUENCE: 11
tggccactca ggagaacgcc ccc                                              23